(12) United States Patent
Lang et al.

(10) Patent No.: US 8,124,621 B2
(45) Date of Patent: Feb. 28, 2012

(54) SUBSTITUTED 1-AMINO-4-PHENYL-DIHYDROISOQUINOLINES, METHODS FOR THE PRODUCTION THEREOF, USE THEREOF AS A MEDICAMENT, AND MEDICAMENTS CONTAINING THEM

(75) Inventors: Hans-Jochen Lang, Frankfurt am Main (DE); John Weston, Frankfurt am Main (DE); Uwe Heinelt, Frankfurt am Main (DE)

(73) Assignee: Sanofi-Aventis, Paris (FR)

( * ) Notice: Subject to any disclaimer, the term of this patent is extended or adjusted under 35 U.S.C. 154(b) by 772 days.

(21) Appl. No.: 12/212,301

(22) Filed: Sep. 17, 2008

(65) Prior Publication Data

US 2009/0118327 A1    May 7, 2009

Related U.S. Application Data

(63) Continuation of application No. PCT/EP2007/001982, filed on Mar. 8, 2007.

(30) Foreign Application Priority Data

Mar. 18, 2006  (DE) .................. 10 2006 012 544

(51) Int. Cl.
*C07D 217/22* (2006.01)
*A61K 31/47* (2006.01)

(52) U.S. Cl. ....................... 514/310; 546/143
(58) Field of Classification Search ............... None
See application file for complete search history.

(56) References Cited

FOREIGN PATENT DOCUMENTS

| WO | WO 02/40449 | 5/2002 |
|----|-------------|--------|
| WO | WO 02/40450 | 5/2002 |
| WO | WO 03/055880 | 7/2003 |
| WO | WO 2004/085404 | 10/2004 |
| WO | WO 2005/028444 | 3/2005 |

OTHER PUBLICATIONS

Hiremath, S. P., et. al., Indian Journal of Chemistry Section B, vol. 41, No. 2, (2002), pp. 394-399 (abstract).

*Primary Examiner* — Zinna Northington Davis
(74) *Attorney, Agent, or Firm* — Scully, Scott, Murphy & Presser, P.C.

(57) ABSTRACT

The present invention relates to compounds useful in the prevention or treatment of various disorders such as acute or chronic renal failure, for impairments of biliary function, for respiratory impairments such as snoring or sleep apneas or for stroke, and pharmaceutical compositions comprising them. More specifically, the compounds of the present invention comprises substituted 1-amino-4-phenyl-dihydroisoquinolines and their derivatives of formula I:

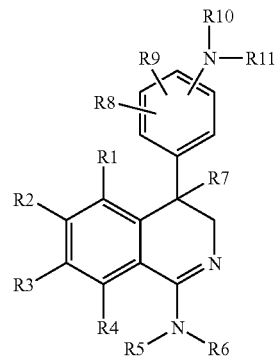

Wherein the substituents R1-R11 are more specifically defined hereinbelow. The claimed compounds of the present invention also include their pharmaceutically acceptable salts and trifluoroacetates thereof as well as methods for their preparation and pharmaceutical delivery systems thereof.

11 Claims, No Drawings

US 8,124,621 B2

SUBSTITUTED 1-AMINO-4-PHENYL-DIHYDROISOQUINOLINES, METHODS FOR THE PRODUCTION THEREOF, USE THEREOF AS A MEDICAMENT, AND MEDICAMENTS CONTAINING THEM

CROSS REFERENCE TO RELATED APPLICATIONS

This application is a continuation of PCT/EP2007/001982 filed on Mar. 8, 2007 which is incorporated herein by reference in its entirety; which claims the benefit of German Patent Application No. 10 2006 012 544.2 filed on Mar. 18, 2006.

FIELD OF THE INVENTION

The present invention relates generally to pharmaceutical compounds and compositions comprising them for the treatment of various renal and respiratory disorders such as acute or chronic renal failure, for impairments of biliary function and respiratory impairments such as snoring, sleep apneas or stroke. More specifically, the present invention relates to compounds of the type of substituted 1-amino-4-phenyl-dihydroquinolines, formulations comprising them and methods for their use.

BACKGROUND OF THE INVENTION

The invention relates generally to novel substituted 1-amino-4-phenyl-dihydroquinolines compounds and compositions comprising them. Pharmaceutical compositions comprising compounds of this type are useful in the prevention or treatment of various disorders. Thus, the compounds can be employed inter alia for renal disorders such as acute or chronic renal failure, for impairments of biliary function, for respiratory impairments such as snoring or sleep apneas or for stroke.

The compounds according to the invention are effective inhibitors of the cellular sodium-proton transporter (Na/H exchanger) which is elevated in numerous disorders (essential hypertension, atherosclerosis, diabetes, etc.), also in those cells which are readily amenable to measurements, such as, for example, in erythrocytes, platelets or leukocytes. The compounds used according to the invention are therefore suitable as excellent and simple scientific tools, for example in their use as diagnostic aids for determining and distinguishing different types of hypertension, but also of atherosclerosis, of diabetes and late complications of diabetes, proliferative disorders etc.

The compounds of the formula I are moreover suitable for preventive therapy to prevent the development and for the treatment of high blood pressure, for example of essential hypertension, because they reduce or completely inhibit the re-absorption of NaCl in the tubular system of the kidneys. Accordingly, they are also outstandingly suitable as combination and formulation partners for drugs used for treating high blood pressure. Examples of possible combinations are diuretics having a thiazide-like action, loop diuretics, aldosterone and pseudo-aldosterone antagonists, such as hydrochlorothiazide, indapamide, polythiazide, furosemide, piretanide, torasemide, bumetamide, amiloride, triamteren. The NHE inhibitors of the present invention can further be used in combination with ACE inhibitors such as, for example, ramipril, enalapril or captopril. Further beneficial combination partners are also β-blockers.

The described NHE inhibitors can likewise be used in the prevention and for the treatment of thrombotic disorders because, as NHE inhibitors, they are able to inhibit both platelet aggregation itself and, in addition, able to inhibit or prevent the excessive release of coagulation mediators, in particular of von Willebrand factor. The NHE inhibitors of the present invention can therefore be combined with further anticoagulant active ingredients such as, for example, acetylsalicylic acid, thrombin antagonists, factor Xa antagonists, drugs with fibrinolytic activity, factor VIIa antagonists etc. Combined use of the present NHE inhibitors with NCBE inhibitors is particularly beneficial.

It has additionally been found that NHE inhibitors show a beneficial effect on serum lipoproteins. It is generally acknowledged that blood lipid levels which are too high, so-called hyper-lipoproteinemias, represent a considerable risk factor for the development of arteriosclerotic vascular lesions, especially coronary heart disease. The reduction of elevated serum lipoproteins therefore has exceptional importance for the prophylaxis and regression of atherosclerotic lesions. The compounds used according to the invention can therefore be used for the prophylaxis and regression of atherosclerotic lesions by eliminating a causal risk factor. The NHE inhibitors of the invention can also be combined in a beneficial manner with other anti-arteriosclerotic active ingredients such as a substance from the class of fibrates, an upregulator of LD2 receptor activity such as MD-700 and LY295427 or a cholesterol or bile acid absorption inhibitor or an anti-hyper-cholesterolemic agent from the class of statins, such as, for example, pravastatin, lovastatin, simvastatin.

With this protection of the vessels against the syndrome of endothelial dysfunction, compounds of the formula I are valuable drugs for the prevention and treatment of coronary vasospasms, peripheral vascular diseases such as intermittent claudication, of atherogenesis and of atherosclerosis, of left-ventricular hypertrophy and of dilated cardiomyopathy, and thrombotic disorders.

It has been possible to show that compounds of the formula I represent excellent inhibitors of the sodium-hydrogen exchanger (NHE), especially of the sodium-hydrogen exchanger of subtype 3 (NHE-3).

NHE-3 inhibitors disclosed to date are derived for example from compounds of the acylguanidine type (EP825178), norbornylamine type (WO0144164), 2-guanidino-quinazoline type (WO0179186) or benzamidine type (WO0121582, WO0172742). Squalamine, which is likewise described as an NHE-3 inhibitor (M. Donowitz et al. Am. J. Physiol. 276 (Cell Physiol. 45): C136-C144), does not according to current knowledge act directly like the compounds of formula I, but acts via an indirect mechanism and thus reaches its maximum strength of effect after only one hour.

Tetrahydroisoquinolines as inhibitors of the sodium-hydrogen exchanger of subtype 3 (NHE-3) are described for example in the patent applications WO03048129, WO2004085404 and the German applications 102004046492.8 and 102005001411.9. The related compound class of tetrahydroisoquinolinium salts is described as NHE-3 inhibitors in the patent application WO03055880.

It has now surprisingly been found that the compounds of the formula I described herein likewise represent potent inhibitors of NHE-3 and moreover have advantageous pharmacological and pharmacokinetic properties.

NHE-3 is found in the body of various species preferentially in the bile, the intestine and the kidney (Larry Fliegel et al, Biochem. Cell. Biol. 76: 735-741, 1998), but has also been detectable in the brain (E. Ma et al. Neuroscience 79: 591-603).

Because of their NHE-inhibitory properties, the compounds of the formula I are suitable for the prevention and treatment of diseases which are caused by activation of or by an activated NHE, and of diseases which are caused secondarily by the NHE-related damage.

The compounds of the formula I can also be employed for the treatment and prevention of diseases where NHE is only partially inhibited, for example by use of a lower dosage.

The use of the compounds of the invention relates to the prevention and treatment of acute and chronic diseases in veterinary and human medicine.

As a consequence of their pharmacological effects, the compounds of the formula I are particularly suitable for leading to an improvement in respiratory drive. They can therefore be used for the treatment of impaired respiratory conditions like those which may occur for example in the following clinical conditions and diseases: impaired central respiratory drive (e.g. central sleep apneas, sudden infant death, postoperative hypoxia), muscle-related respiratory impairments, respiratory impairments following long-term ventilation, respiratory impairments associated with adaptation to high altitude, obstructive and mixed form of sleep apneas, acute and chronic pulmonary diseases with hypoxia and hypercapnia. In addition, the compounds increase the tone of the muscles of the upper airways, so that snoring is suppressed. Said compounds are therefore advantageously used for the manufacture of a medicament for the prevention and treatment of sleep apneas and muscle-related respiratory impairments and for the manufacture of a medicament for the prevention and treatment of snoring.

SUMMARY OF THE INVENTION

The present invention relates to compounds useful in the prevention or treatment of various disorders such as acute or chronic renal failure, for impairments of biliary function, for respiratory impairments such as snoring or sleep apneas or for stroke, and pharmaceutical compositions comprising them. More specifically, the compounds of the present invention comprises substituted 1-amino-4-phenyl-dihydroisoquinolines and their derivatives of formula I:

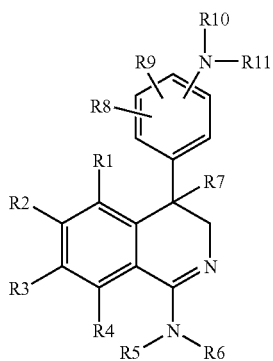

Wherein the substituents R1-R11 are more specifically defined hereinbelow. The claimed compounds of the present invention also include their pharmaceutically acceptable salts and trifluoroacetates thereof as well as methods for their preparation and pharmaceutical delivery systems thereof.

DETAILED DESCRIPTION OF THE INVENTION

As noted above, the present invention comprises pharmaceutically active compounds and compositions comprising them consisting of substituted 1-amino-4-phenyl-dihydroisoquinolines and their derivatives of formula I:

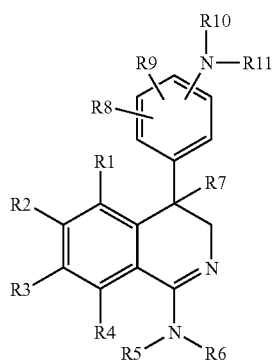

wherein:
R1, R2, R3 and R4 are independently selected from the group consisting of hydrogen, F, Cl, Br, I, CN, $NO_2$, $CF_3$, $CH_3$—$SO_2$, alkyl having 1, 2, 3 or 4 carbon (C) atoms, $NH_2$, NH—$CH_3$ or $N(CH_3)_2$;

R5 and R6 are independently selected from the group consisting of hydrogen, alkyl having 1, 2, 3, 4, 5 or 6 C atoms, $CF_3$—$CH_2$—, cycloalkyl having 3, 4, 5 or 6 C atoms or cyclopropyl-$CH_2$—, or R5 and R6, together with the nitrogen atom to which they are bonded, form a 4-, 5-, 6-, 7-, 8-, 9- or 10-membered ring in which one or two $CH_2$ groups may be replaced independently of one another by NR12, sulfur, oxygen, C(O) or $SO_2$;

and

R12 is a hydrogen, alkyl having 1, 2, 3 or 4 C atoms or cycloalkyl having 3, 4, 5 or 6 C atoms;

R7 is hydrogen or an alkyl having 1, 2, 3 or 4 C atoms;

R8 and R9 are independently selected from the group consisting of hydrogen, F, Cl, Br, OH, alkyl having 1, 2, 3 or 4 C atoms, $CH_3O$, $CF_3$, or $CH_3SO_2$;

R10 and 11 are independently R13-$(C_mH_{2m})$—$B_n$, where
m zero, 1, 2, 3 or 4;
n zero or 1;
B —CO—, —CONR14- or —$SO_2$—; and,
R14 is hydrogen or alkyl having 1, 2, 3, 4, 5 or 6 C atoms; and,
R13 is selected from the group consisting of hydrogen, alkyl having 1, 2, 3 or 4 C atoms, cycloalkyl having 3, 4, 5 or 6 C atoms, 1-pyrrolidinyl, 1-piperidinyl, 1-(4-methylpiperazinyl), 1-morpholinyl, —COOR15, OR16, NR17R18 or phenyl which has independently of one another 1 or 2 substituents selected from the group of chlorine, fluorine, methyl and methoxy; and,
R15, R16, R17 and R18 are hydrogen or alkyl having 1, 2, 3, 4, 5 or 6 C atoms;

or

R10 and R11, together with the nitrogen atom to which they are bonded, form a 4-, 5-, 6-, 7-, 8-, 9- or 10-membered ring in which one, two, three or four $CH_2$ groups may be replaced independently of one another by NR19, sulfur, oxygen, C(O) or $SO_2$;

R19 hydrogen, alkyl having 1, 2, 3 or 4 C atoms or cycloalkyl having 3, 4, 5 or 6 C atoms; and the pharmaceutically acceptable salts and trifluoroacetates thereof.

Preferably, the present invention comprises compounds of formula I in which
R1, R2, R3 and R4 are selected from the group consisting of
hydrogen, F, Cl, Br, CN, $CF_3$, $CH_3$—$SO_2$, alkyl having 1, 2, 3 or 4 C atoms, $NH_2$, NH—$CH_3$ and $N(CH_3)_2$;
R5 and R6 are independently selected from the group consisting of hydrogen, alkyl having 1, 2, 3, 4, 5 or 6 C atoms, $CF_3$—$CH_2$—, cycloalkyl having 3, 4, 5 or 6 C atoms and cyclopropyl-$CH_2$—,
or
R5 and R6, together with the nitrogen atom to which they are bonded, form a 4-, 5-, 6-, 7-, 8-, 9- or 10-membered ring;
R7 is hydrogen or methyl;
R8 and R9 are independently selected from the group consisting of hydrogen, F, Cl, OH, alkyl having 1, 2, 3 or 4 C atoms, $CH_3O$, $CF_3$, and or $CH_3SO_2$;
R10 and 11 are independently selected from the group consisting of R13-$(C_mH_{2m})$—$B_n$, where
m zero, 1, 2, 3 or 4;
n zero or 1;
B —CO—, —CONR14- or —$SO_2$—; and,
R14 is hydrogen or alkyl having 1, 2, 3, 4, 5 or 6 C atoms; and,
R13 is selected from the group consisting of hydrogen, an alkyl having 1, 2, 3 or 4 C atoms, cycloalkyl having 3, 4, 5 or 6 C atoms, 1-pyrrolidinyl, 1-piperidinyl, 1-(4-methylpiperazinyl), 1-morpholinyl, —COOR15, OR16, NR17R18 or phenyl which has independently of one another 1 or 2 substituents selected from the group of chlorine, fluorine, methyl and methoxy;
R15, R16, R17 and R18 are hydrogen or alkyl having 1, 2, 3, 4, 5 or 6 C atoms;
or
R10 and R11, together with the nitrogen atom to which they are bonded, form a 4-, 5-, 6-, 7-, 8-, 9- or 10-membered ring in which one, two, three or four $CH_2$ groups may be replaced independently of one another by NR19, sulfur, oxygen, C(O) or $SO_2$;
R19 is a hydrogen or alkyl having 1, 2, 3 or 4 C atoms; and.
the pharmaceutically acceptable salts and trifluoroacetates thereof.

More preferably, compounds of the present invention comprise those of formula I in which
R1, R2, R3 and R4 are independently selected from the group consisting of hydrogen, F, Cl, Br, CN, $CF_3$, $CH_3$—$SO_2$, methyl, ethyl, $NH_2$, NH—$CH_3$ and $N(CH_3)_2$;
R5 and R6 are independently selected from the group consisting of hydrogen, methyl, ethyl, isopropyl, $CF_3$—$CH_2$ or cycloalkyl having 3, 4, 5 and 6 C atoms;
or
R5 and R6, together with the nitrogen atom to which they are bonded, form a 4-, 5-, 6-, 7-, 8-, 9- or 10-membered ring;
R7 hydrogen or methyl;
R8 and R9 are independently hydrogen, Cl or methyl;
R10 and 11 are independently selected from the group consisting of
R13-$(C_mH_{2m})$—$B_n$, where
m zero, 1, 2, 3 or 4;
n zero or 1;
B —CO—, —CONR14- or —$SO_2$—; and
R14 is a hydrogen or alkyl having 1, 2, 3, 4, 5 or 6 C atoms;
R13 is a hydrogen, methyl, ethyl, isopropyl, cycloalkyl having 3, 4, 5 or 6 C atoms, 1-pyrrolidinyl, 1-piperidinyl, 1-(4-methylpiperazinyl), —COOR15, OR16 or NR17R18;
R15, R16, R17 and R18 are independently selected from the group consisting of hydrogen or alkyl having 1, 2, 3, 4, 5 or 6 C atoms;
or
R10 and R11, together with the nitrogen atom to which they are bonded a 4-, 5-, 6-, 7-, 8-, 9- or 10-membered ring, in which one, two or three $CH_2$ groups may be replaced independently of one another by NR19 or C(O); and
R19 is hydrogen or methyl; and,
the pharmaceutically acceptable salts and trifluoroacetates thereof.

Even more preferably, the present invention comprises compounds of formula I in which:
R1 and R3 are hydrogen;
R2 and R4 are independently of one another hydrogen or Cl;
R5 and R6 are independently hydrogen or methyl;
or
R5 and R6, together with the nitrogen atom to which they are bonded, form a 5- or 6-membered ring;
R7 is hydrogen;
R8 and R9 are independently hydrogen or Cl;
R10 and 11 are independently R13-$(C_mH_{2m})$—$B_n$, where
m zero, 1, 2, 3 or 4;
n zero or 1;
B —CO— or —CONR14-; and wherein
R14 is hydrogen or methyl;
R13 is selected from the group consisting of hydrogen, methyl, cycloalkyl having 3, 4, 5 or 6 C atoms, 1-pyrrolidinyl, 1-piperidinyl, 1-(4-methylpiperazinyl), —COOR15, OR16 or NR17R18; and,
R15, R16, R17 and R18 are independently hydrogen or an alkyl having 1, 2, 3, 4, 5 or 6 C atoms;
or
R10 and R11, together with the nitrogen atom to which they are bonded, form a 4-, 5-, 6-, 7-, 8-, 9- or 10-membered ring in which one, two or three $CH_2$ groups may be replaced independently of one another by NR19, or C(O) and wherein R19 is a hydrogen or methyl; and,
the pharmaceutically acceptable salts and trifluoroacetates thereof.

Even more preferably, the present invention comprises compounds of formula I in which:
R1 and R3 are hydrogen;
R2 and R4 are independently hydrogen or Cl;
R5 and R6 are independently hydrogen or methyl;
or
R5 and R6, together with the nitrogen atom to which they are bonded, form a 5- or 6-membered ring;
R7 is hydrogen;
R8 and R9 are independently hydrogen or Cl;
R10 and 11 are independently R13-$(C_mH_{2m})$—$B_n$, wherein
m zero, 1, 2, 3 or 4;
n zero or 1;
B —CONR14-; and,
R14 is hydrogen or methyl;
R13 is hydrogen, methyl, or COOR15 wherein R15 is hydrogen, methyl or ethyl;
or
R10 and R11, together with the nitrogen atom to which they are bonded, form a 4-, 5-, 6-, 7-, 8-, 9- or 10-membered ring in which one, two or three $CH_2$ groups may be replaced independently by NR19 or C(O);
wherein R19 is a hydrogen or methyl;
and the pharmaceutically acceptable salts and trifluoroacetates thereof.

Most preferably compounds of the present invention comprise those of formula I selected from the group comprising:

1-amino-4-(4-aminophenyl)-6-chloro-3,4-dihydroisoquinoline,
1-amino-4-(4-aminophenyl)-3,4-dihydroisoquinoline,
1-amino-4-(2-aminophenyl)-6-chloro-3,4-dihydroisoquinoline,
4-(4-aminophenyl)-6-chloro-1-methylamino-3,4-dihydroisoquinoline,
4-(4-aminophenyl)-6-chloro-1-dimethylamino-3,4-dihydroisoquinoline,
4-(4-aminophenyl)-6-chloro-1-(N-pyrrolidino)-3,4-dihydroisoquinoline,
N-(ethoxycarbonylmethyl)-N'-4-[(6-chloro-3,4-dihydro-1-dimethylaminoisoquinolin-4-yl)phenyl]urea
and
3-{4-[(6-chloro-3,4-dihydro-1-dimethylaminoisoquinolin-4-yl)phenyl]}imidazolidine-2,4-dione
and the pharmaceutically acceptable salts and trifluoroacetates thereof.

In one embodiment, preferred compounds of the formula I are those in which the radicals R1, R2, R3 and R4 are independently selected from the group consisting of hydrogen, F, Cl, Br, CN, $CF_3$, $CH_3$—$SO_2$, alkyl having 1, 2, 3 or 4 C atoms, for example methyl or ethyl, $NH_2$, NH—$CH_3$ or $N(CH_3)_2$; particularly preferred compounds of the formula I are those in which R1 and R3 are hydrogen and R2 and R4 are independently of one another hydrogen, F, Cl, Br, CN, $CF_3$, $CH_3$—$SO_2$, methyl, ethyl, $NH_2$, NH—$CH_3$ or $N(CH_3)_2$, for example hydrogen or Cl; in a further embodiment, preferred compounds of the formula I are those in which R1, R3 and R4 are hydrogen, and R2 is F, Cl, Br, CN, $CF_3$, $CH_3$—$SO_2$, methyl, ethyl, $NH_2$, NH—$CH_3$ or $N(CH_3)_2$, for example Cl.

In another embodiment, preferred compounds of the formula I are those in which R5 and R6 are described independently of one another by hydrogen, alkyl having 1, 2, 3, 4, 5 or 6 C atoms, $CF_3$—$CH_2$— or cycloalkyl having 3, 4, 5 or 6 C atoms, or R5 and R6 form together with the nitrogen atom to which they are bonded a 4-, 5-, 6-, 7-, 8-, 9- or 10-membered ring; in a further embodiment, preferred compounds of the formula I are those in which R5 and R6 are independently of one another hydrogen, methyl, ethyl, isopropyl, $CF_3$—$CH_2$ or cycloalkyl having 3, 4, 5 or 6 C atoms, or R5 and R6 form together with the nitrogen atom to which they are bonded a 4-, 5-, 6-, 7-, 8-, 9- or 10-membered ring; particularly preferred compounds of the formula I are those in which R5 and R6 are hydrogen, methyl or ethyl, for example hydrogen or methyl, or R5 and R6 form together with the nitrogen atom to which they are bonded a 5- or 6-membered ring, especially pyrrolidine or piperidine, for example pyrrolidine.

In yet another embodiment, preferred compounds of formula I are those in which R7 is hydrogen or methyl, for example hydrogen.

In one embodiment, preferred compounds of the formula I are those in which the radicals R8 and R9 are described independently of one another by hydrogen, F, Cl, OH, alkyl having 1, 2, 3 or 4 C atoms, $CH_3O$, $CF_3$, or $CH_3SO_2$; particularly preferred compounds of the formula I are those in which R8 and R9 are described independently of one another by hydrogen, Cl or methyl, in particular hydrogen or Cl, for example hydrogen.

The radical NR10R11 on the phenyl ring may be bonded in the position ortho, meta or para to the dihydroisoquinoline group, for example in the ortho- or para-position, in particular in the para-position.

In one embodiment, preferred compounds of the formula I are those in which the radicals R10 and R11 are described independently of one another by R13-($C_mH_{2m}$)—$B_n$ or R10 and R11 form together with the nitrogen atom to which they are bonded a 4-, 5-, 6-, 7-, 8-, 9- or 10-membered ring in which one, two or three $CH_2$ groups may be replaced by NR19 or C(O), where R19 is hydrogen or alkyl having 1, 2, 3 or 4 C atoms, in particular hydrogen or methyl; in a further embodiment, preferred compounds of the formula I are those in which the radicals R10 and R11 are described independently of one another by R13-($C_mH_{2m}$)—$B_n$. In a further embodiment, preferred compounds of the formula I are those in which R10 and R11 form together with the nitrogen atom to which they are bonded a 4-, 5-, 6-, 7-, 8-, 9- or 10-membered ring in which one, two or three $CH_2$ groups may be replaced by NR19 or C(O), for example 3 $CH_2$ groups replaced by one NR19 and two C(O), where R19 is hydrogen or methyl;

In one embodiment, preferred compounds of the formula I are those in which m is zero, 1 or 2, for example zero or 1.

In one embodiment, preferred compounds of the formula I are those in which n is zero; in a further embodiment, preferred compounds of the formula I are those in which n is 1.

In one embodiment, preferred compounds of the formula I are those in which B is —CO— or —CONR14-, in particular —CONR14-, where R14 is hydrogen or alkyl having 1, 2, 3, 4, 5 or 6 C atoms, in particular hydrogen or methyl, for example hydrogen.

In one embodiment, preferred compounds of the formula I are those in which R13 is described by hydrogen, methyl, ethyl, isopropyl, cycloalkyl having 3, 4, 5 or 6 C atoms, 1-pyrrolidinyl, 1-piperidinyl, 1-(4-methylpiperazinyl), —COOR15, OR16 or NR17R18, where R15, R16, R17 and R18 are independently of one another hydrogen or alkyl having 1, 2, 3, 4, 5 or 6 C atoms; in a further embodiment, preferred compounds of the formula I are those in which R13 is described by hydrogen, methyl or —COOR15, where R15 is hydrogen or alkyl having 1, 2, 3, 4, 5 or 6 C atoms, in particular hydrogen, methyl or ethyl, for example ethyl; particularly preferred compounds of the formula I are those in which R13 is hydrogen or —COOR15, where R15 is ethyl.

If the compounds of the formula I comprise one or more asymmetric centers, these may independently of one another have either the S or the R configuration. The compounds may be in the form of optical isomers, of diastereomers, racemates or mixtures thereof. The compounds of the formula I may moreover be in the form of rotational isomers.

The present invention includes all tautomeric forms of the compounds of formula I.

The present invention further includes derivatives of the compounds of the formula I, for example solvates such as hydrates and alcohol adducts, esters, prodrugs and other physiologically acceptable derivatives of the compounds of the formula I, and active metabolites of the compounds of the formula I. The invention likewise includes all crystal modifications of the compounds of the formula I.

Alkyl radicals may be straight-chain or branched. This also applies when they have substituents or occur as substituents of other radicals, for example in fluoroalkyl radicals or alkoxy radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), n-pentyl, isopentyl, tert-pentyl, neopentyl or hexyl. Preferred alkyl radicals are methyl, ethyl, n-propyl, isopropyl, n-butyl, tert-butyl, n-pentyl, n-hexyl.

Examples of cycloalkyl radicals are cyclopropyl, cyclobutyl, cyclopentyl, cyclohexyl, cycloheptyl or cyclooctyl. One or more $CH_2$ groups in the cycloalkyl radicals may be replaced by O, NH or N-alkyl, for example $NCH_3$. This also applies to cycloalkylmethyl radicals.

Examples of NR5R6 rings are morpholine, pyrrolidine, piperidine, piperazine, N-methylpiperazine, pyrrolidin-2-one, pyrrolidine-2,5-dione, imidazolidine, 3-methylimidazolidine, imidazolidin-2-one, 3-methylimidazolidin-2-one, imidazolidine-2,4-dione and 1-methylimidazolidine-2,4-dione, especially pyrrolidine and piperidine, for example pyrrolidine.

Examples of NR10R11 rings are morpholine, pyrrolidine, piperidine, piperazine, N-methylpiperazine, pyrrolidin-2-one, pyrrolidine-2,5-dione, imidazolidine, 3-methylimidazolidine, imidazolidin-2-one, 3-methylimidazolidin-2-one, imidazolidine-2,4-dione and 1-methylimidazolidine-2,4-dione, especially pyrrolidine-2,5-dione and imidazolidine-2,4-dione, for example imidazolidine-2,4-dione.

The terminal $CH_3$ groups in an alkyl radical are also regarded as $CH_2$ units and, in this connection, are understood as $CH_2$—H groups.

If a variable, for example cycloalkyl or R1, occurs more than once as component, the substituents that comprise the variables are independent of one another at each occurrence.

If the compounds of the formula I comprise one or more acidic or basic groups or one or more basic heterocycles, the invention also includes the corresponding physiologically or toxicologically acceptable salts, in particular the pharmaceutically usable salts. Thus, the compounds of the formula I may be deprotonated on an acidic group and be used for example as alkali metal salts, preferably sodium or potassium salts, or as ammonium salts, for example as salts with ammonia or organic amines or amino acids. Since compounds of the formula I always comprise at least one basic group, they can also be prepared in the form of their physiologically tolerated acid addition salts, e.g. with the following acids: from inorganic acids such as hydrochloric acid, sulfuric acid or phosphoric acid or from organic acids such as acetic acid, citric acid, tartaric acid, lactic acid, malonic acid, methanesulfonic acid, fumaric acid. Suitable acid addition salts in this connection are salts of all pharmacologically acceptable acids (this group also corresponds to the physiologically acceptable anions), for example halides, especially hydrochlorides, lactates, sulfates, citrates, tartrates, acetates, phosphates, methylsulfonates, p-toluenesulfonates, adipates, fumarates, gluconates, glutamates, glycerophosphates, maleates and pamoates, but also trifluoroacetates.

The invention also relates to the process described below for preparing the compounds of the formula I.

The compounds of the formula I in which R10 and R11 are hydrogen and which are described herein can be prepared for example starting from nitrophenyl derivatives of the formula II by reduction to the corresponding amino compounds of the formula Ia where the substituents R1, R2, R3, R4, R5, R6, R8 and R9 are defined above. The reduction can take place by processes known to the skilled worker using a large number of reducing agents, including catalytic hydrogenation, for example by catalytic hydrogenation or with an inorganic reducing agent such as, for example, with iron powder and hydrochloric acid in glacial acetic acid.

Other preferred compounds of the present invention the formula I can be prepared from the compounds according to the invention of the formula I a) for example by derivatization of the amino group on the phenyl radical by processes known to the skilled worker. In these cases, for example, the amino group of the compounds Ia) is reacted with alkylating agents, acylating agents or sulfonylating reagents of the formula R10-L and/or R11-L, advantageously in the presence of an auxiliary base, such as pyridine, triethylamine or Hünig's base, in a manner known to the skilled worker. It is likewise suitable to use isocyanates of the formulae R10-N=C=O and/or R11-N=C=O in a manner known in the art for preparing corresponding urea derivatives of the formula Ib or Ic

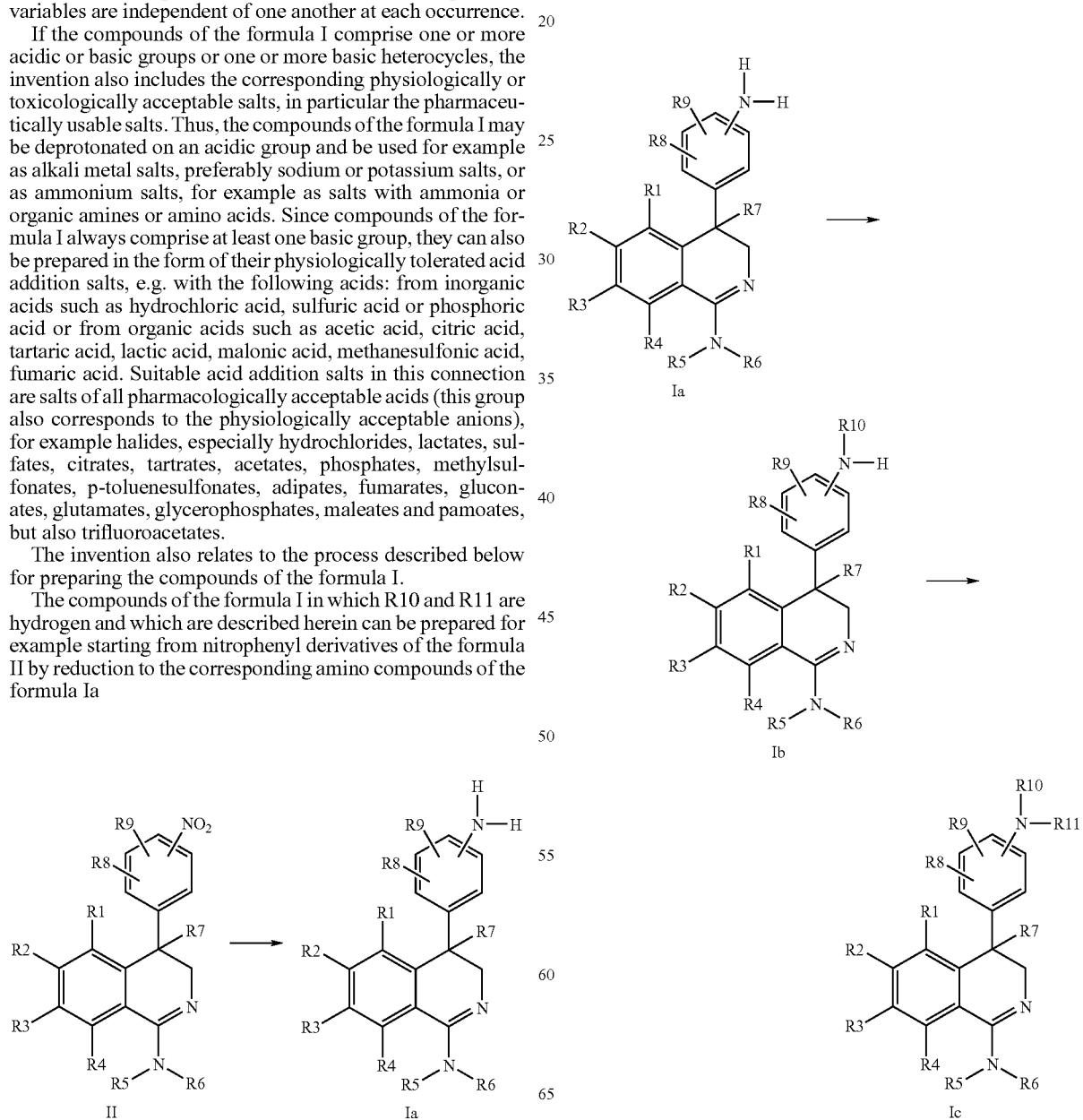

where the substituents R1, R2, R3, R4, R5, R6, R8, R9, R10 and R11 have the meaning indicated above, but R10 and R11 are not hydrogen, and L is F, Cl, Br, I, —OR, —OC(O)R or —SR, where R is alkyl having 1, 2, 3, 4, 5 or 6 C atoms, for example methyl or ethyl, and L may be —SR when B is —C(O)—. It is possible by reactions taking place stepwise for example for the monosubstituted compound of the invention of the formula Ib to be obtained and isolated and/or subsequently reacted to give the disubstituted compound of the formula Ic.

The compounds of the formula IV can be converted in various ways, for example by nucleophilic exchange with compounds of the formula III by processes known in the art into compounds of the formula II

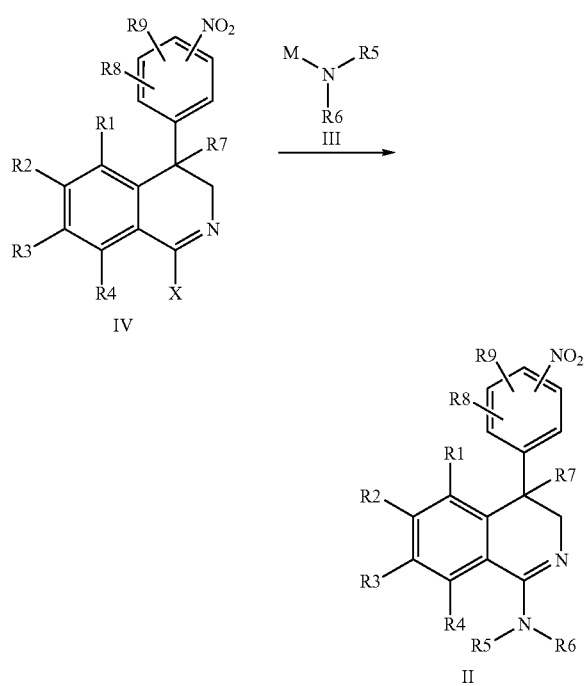

where R1, R2, R3, R4, R5, R6, R8, R9 and Y have the meaning indicated above, but R5 and R6 are not both hydrogen, X represents a leaving group able to undergo nucleophilic substitution, such as, for example, chloride, bromide, tosylate, mesylate, triflate, alkoxy having 1, 2, 3, 4, 5 or 6 C atoms, for example ethoxy, aryloxy, for example phenoxy, or R'S(O)$_n$— where n is 0 or 2, and R' is an alkyl radical, preferably having 1, 2, 3 or 4 C atoms, for example, methyl, and M is either hydrogen or a metal, in particular an alkali metal or an alkaline earth metal equivalent, for example lithium, or the compound VII is a Grignard compound. It is advantageous to employ temperatures of >100° C. with amines, it being possible to recommend the use of an autoclave or a microwave.

Corresponding compounds of the formula IVb in which R5 and R6 are hydrogen can be prepared analogously by reaction with NH$_3$ and under pressure.

The compounds of the formula IVa with X=R'—S— can be obtained by processes known in the art by reacting the corresponding mercapto compounds of the formula V with an alkylating agent of the formula VI

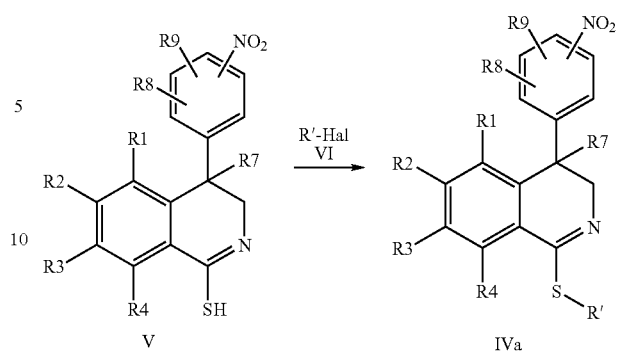

where R1, R2, R3, R4, R7, R8 and R9 have the meaning indicated above, R' is an alkyl radical, preferably having 1, 2, 3 or 4 C atoms, for example methyl, and Hal is chlorine, bromine or iodine.

Compounds of the formula V can be prepared for example by acid-catalyzed cyclization of the corresponding isothiocyanates of the formula VIII by processes known in the art.

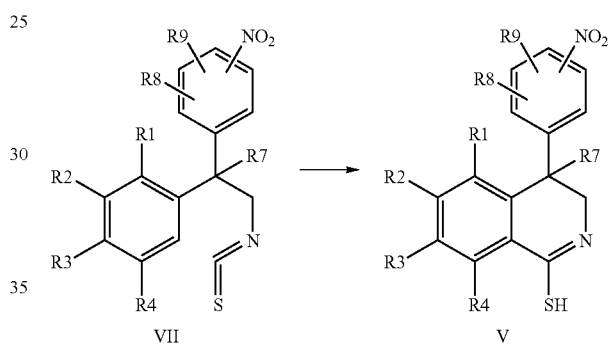

where the substituents R1, R2, R3, R4, R7, R8 and R9 have the meaning indicated above. Acids which can be used are both protic and aprotic Lewis acids. It has proved advantageous to use concentrated sulfuric acid for the present cyclization.

The isothiocyanates of the formula VII can be prepared by a process known to the skilled worker from the corresponding amines of the formula VIII with a thiocarbonylating agent, for example thiophosgene S=CCl$_2$ or thiocarbonylbisimidazole

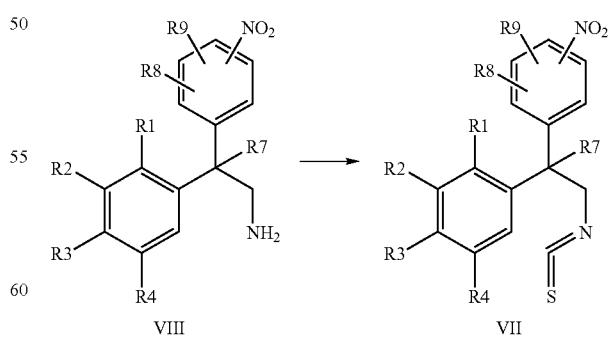

where the substituents R1, R2, R3, R4, R7, R8 and R9 have been previously defined above.

The phenethylamine precursors of formula VIII, if not obtainable by purchase, can be obtained by standard processes known in the art, for example, from the corresponding nitriles of the formula IX by reduction

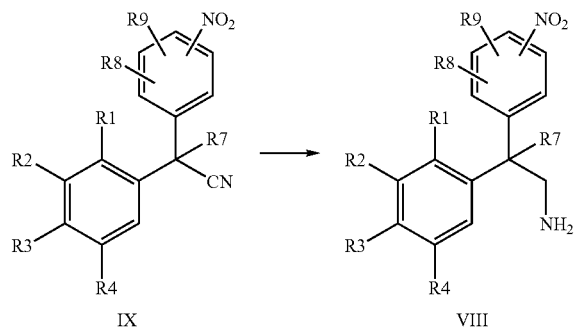

where the substituents R1, R2, R3, R4, R7, R8 and R9 have been previously defined above. Boron-hydrogen complexes are useful for this reduction, because they leave the nitro group unaffected and it can then later be reduced, separately and selectively, for example with iron powder, to the anilino group (Umino, Tetrahedron Letters 33: 2875-76 (1976), J. Org. Chem. 53, 98-104 (1988), Org. Prep. Proced. Int. 13:225 (1981), J. Org. Chem. 47:1389 (1982), Chem. Rev. 76:773 (1973)). which is hereby incorporated herein by reference.

The compounds of the formula IX can either be purchased commercially or prepared by various processes known to those skilled in the art. Thus, for example, it is possible to start with compounds of formula XI and convert them in a manner known by those skilled in the art by means of a base by generating the anion of the formula X in a nucleophilic substitution reaction on the aromatic moiety with a compound of the formula XII

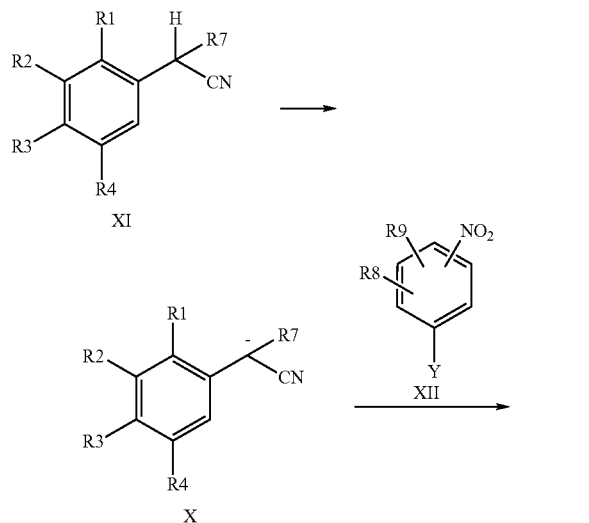

where the substituents R1, R2, R3, R4, R7, R8 and R9 have been previously defined above, Y is a nucleophilically replaceable radical, for example chloride, fluoride, bromide, $NO_2$, triflate or mesylate, and for conversion of the compound of the formula XI to the compound of the formula X a desired base, for example $HO^-$, $CH_3$—$O^-$ or tert-but-$O^-$, LDA, $NaNH_2$ or $K(N(SiMe_3)_2)$, is used. Normal alkali metal hydroxide solution has proved advantageous in this reaction under the conditions of two-phase catalysis, using as two-phase catalyst for example N-benzyl-N,N,N-triethylammonium chloride. (DE2610837).

Introduction of a radical R7 which is not hydrogen is possible by processes known to those skilled in the art also at a later stage. For example, the compound of the formula IXa can be deprotonated with a sufficiently strong base and then reacted with an alkylating agent of the formula XIII

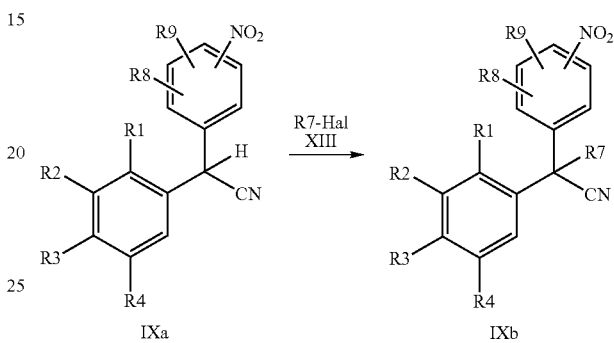

where the substituents R1, R2, R3, R4, R7, R8 and R9 and Hal have been hereinbefore defined above.

Introduction of the nitro group is also possible in a known manner at a later stage, for example, by direct nitration reaction of a compound of the formula XIV with nitric acid or a nitronium generator such as, for example $[NO_2^+SbF_6^-]$

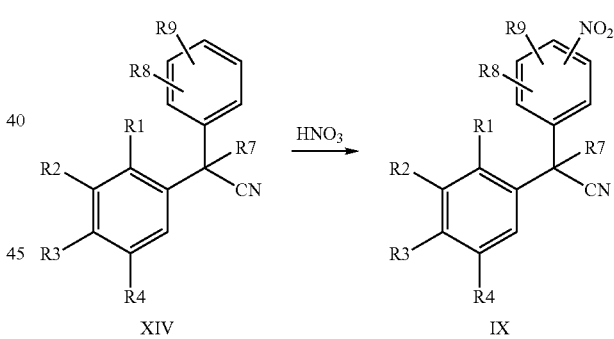

where the substituents R1, R2, R3, R4, R7, R8 and R9 have been hereinbefore defined above.

The compounds R10-Hal, R11-Hal, R10-N=C=O, R11-N=C=O and the compounds of the formulae III, VI, XI, XII, XIII and XIV can be obtained by purchase or can be prepared by or in analogy to processes described in the literature and known in the art. The compounds of the formula IV or IVa can be obtained by purchase, can be prepared by the processes described above (for X=alkyl-S—) or can be prepared by or in analogy to processes described in the literature. The compounds of the formulae VIII, IX and IXa can be obtained by purchase, can be prepared by the processes described above or can be prepared by or in analogy to processes described in the literature and known in the art.

The preparation and the purification of the products and/or intermediates takes place by the usual methods such as extraction, chromatography or crystallization and the usual dryings.

NHE3 inhibitors disclosed to date are derived for example from compounds of the acylguanidine type (EP825178), norbornylamine type (WO0144164), 2-guanidino-quinazoline type (WO0179186) or benzamidine type (WO0121582, WO0172742). Squalamine, which is likewise described as an NHE3 inhibitor (M. Donowitz et al. Am. J. Physiol. 276 (Cell Physiol. 45): C136-C144), does not according to current knowledge act directly like the compounds of formula I, but acts via an indirect mechanism and thus reaches its maximum strength of effect after only one hour.

Tetrahydroisoquinolines as inhibitors of the sodium-hydrogen exchanger of subtype 3 (NHE3) are described for example in the patent applications WO03048129, WO2004085404 and the German applications 102004046492.8 and 102005001411.9. The related compound class of tetrahydroisoquinolinium salts is described as NHE3 inhibitors in the patent application WO03055880.

It has now surprisingly been found that the compounds of the formula I described herein likewise represent potent inhibitors of NHE3 and moreover have advantageous pharmacological and pharmacokinetic properties.

NHE3 is found in the body of various species preferentially in the bile, the intestine and the kidney (Larry Fliegel et al, Biochem. Cell. Biol. 76: 735-741, 1998), but has also been detectable in the brain (E. Ma et al. Neuroscience 79: 591-603).

Because of their NHE-3-inhibitory properties, the compounds of the formula I are suitable for the prevention and treatment of diseases which are caused by activation of or by an activated NHE, and of diseases which are caused secondarily by the NHE-related damage.

The compounds of the formula I can also be employed for the treatment and prevention of diseases where NHE-3 is only partially inhibited, for example by use of a lower dosage.

The combination of an NHE-3 inhibitor of formula I with a carbonic anhydrase inhibitor (e.g. acetazolamide) may also be advantageous, the latter bringing about a metabolic acidosis and thus itself increasing respiratory activity, so that an enhanced effect and reduced use of active ingredient can be achieved.

The compounds of the invention preserve, as a result of their NHE3-inhibitory effect, the cellular energy reserves which are rapidly exhausted during toxic and pathogenic events and thus lead to cell damage or cell death. In this connection, the energy-costly ATP-consuming sodium absorption in the proximal tubule temporarily ceases under the influence of NHE3 inhibitors, and the cell is thus able to survive an acute pathogenic, ischemic or toxic situation. The compounds are therefore suitable for example as pharmaceuticals for the treatment of ischemic noxae, for example of acute renal failure. The compounds are further suitable also for the treatment of all chronic renal disorders and types of nephritis which lead, as a consequence of increased protein excretion, to chronic renal failure. Accordingly, the compounds of the formula I are suitable for the manufacture of a medicament for the treatment of late damage from diabetes, of diabetic nephropathy and of chronic renal disorders, in particular of all renal inflammations (nephritides) which are associated with an increased protein/albumin excretion.

The compounds of the present invention may also have a mild laxative effect and accordingly can also be used advantageously as laxatives or if there is a risk of constipation.

The compounds of the present invention can also be used for the prevention and therapy of acute and chronic disorders of the intestinal tract which are induced by ischemic states in the intestinal region and/or by subsequent reperfusion or by inflammation. Such complications may arise for example through deficient intestinal peristalsis as are frequently to be observed for example following surgical interventions, associated with constipation or greatly reduced intestinal activity.

It is possible with the compounds of the invention to prevent the formation of gallstones.

The NHE inhibitors of the invention are also suitable for the treatment of diseases caused by ischemia and by reperfusion.

The compounds of the invention are, as a result of their pharmacological properties, suitable as anti-arrhythmic pharmaceuticals. Due to their cardioprotective component, the NHE-3 inhibitors of the present invention are also useful in the treatment of infarction and for the treatment of infarction, and for the treatment of angina pectoris, in which case they inhibit or greatly reduce preventively the pathophysiological processes associated with the development of damage induced by ischemia, in particular with the triggering of cardiac arrhythmias induced by ischemia. Because of their protective effects against pathological hypoxic and ischemic situations, the compounds of the formula I used according to the invention can, as a result of inhibition of the cellular $Na^+/H^+$ exchange mechanism, be used as pharmaceuticals for the treatment of all acute or chronic damage induced by ischemia or diseases induced primarily or secondarily thereby.

The compounds are also useful as pharmaceuticals in surgical interventions. Thus, the compounds of the invention can be used in organ transplantations, in which case the compounds can be used both to protect the organs in the donor before and during removal, to protect removed organs for example during treatment with or storage thereof in physiological bath fluids, as well as during transfer into the recipient organism pre-treated with compounds of the formula I.

The compounds are likewise valuable pharmaceuticals with a protective effect for carrying out angioplastic surgical interventions for example on the heart as well as on peripheral organs and vessels.

The compounds of the invention can also be used when performing bypass operations, for example in bypass operations on coronary vessels and in coronary artery bypass graft (CABG).

In accordance with their effect against damage induced by ischemia, the compounds of the invention of the formula I can also be employed in resuscitation following cardiac arrest.

In accordance with their protective effect against damage induced by ischemia, the compounds are also suitable as pharmaceuticals for the treatment of ischemias of the nervous system, especially of the CNS, being suitable for example for the treatment of stroke or of cerebral edema.

Since NHE inhibitors of human tissue and organs protect effectively not only against damage caused by ischemia and reperfusion but also against the cytotoxic effect of pharmaceuticals like those used in particular in cancer therapy and the therapy of autoimmune diseases, combined administration thereof with compounds of the formula I is suitable for reducing or suppressing the cytotoxic effects of a therapy. The reduction in the cytotoxic effects, especially the cardiotoxicity, as a result of comedication with NHE inhibitors makes it additionally possible to increase the dose of the cytotoxic therapeutic agents and/or to prolong the medication with such pharmaceuticals. The therapeutic benefit of such a cytotoxic therapy can be increased considerably by combination with NHE inhibitors.

The compounds of the formula I are particularly suitable for improving therapy with pharmaceuticals which have an unwanted cardiotoxic component.

In general, the NHE inhibitors described herein can beneficially be combined with other compounds which likewise regulate the intracellular pH, those suitable being inhibitors of the enzyme group of carbonic anhydratases, inhibitors of systems which transport bicarbonate ions, such as the sodium-bicarbonate cotransporter (NBC) or the sodium-dependent chloride-bicarbonate exchanger (NCBE), and with other NHE inhibitors having an inhibitory effect on other NHE subtypes, as combination partners, because they may enhance or modulate the pharmacologically relevant pH-regulating effects of the NHE inhibitors described herein.

In accordance with their protective effect against damage induced by ischemia, the compounds are also suitable as pharmaceuticals for the treatment of ischemias of the nervous system, especially of the central nervous system, being suitable for example for the treatment of stroke or of cerebral edema.

The compounds of the formula I are also suitable for the therapy and prophylaxis of disorders and impairments induced by overexcitability of the central nervous system, in particular for the treatment of epileptiform disorders, centrally induced clonic and tonic spasms, states of mental depression, anxiety disorders and psychoses. The NHE inhibitors of the invention may in this connection be used alone or in combination with other substances having antiepileptic activity or antipsychotic active ingredients, or carbonic anhydratase inhibitors, for example with acetazolamide, and with further inhibitors of NHE or of the sodium-dependent chloride-bicarbonate exchanger (NCBE).

In addition, the compounds of the invention of the formula I are likewise suitable for the treatment of types of shock such as, for example, of allergic, cardiogenic, hypovolemic and bacterial shock.

The compounds of the formula I can likewise be used for the prevention and treatment of thrombotic disorders because, as NHE inhibitors, they are able to inhibit both platelet aggregation itself. In addition, they are able to inhibit or prevent the excessive release of mediators of inflammation and coagulation, in particular of von Willebrand factor and thrombogenic selectin proteins, which takes place following ischemia and reperfusion. It is thus possible to reduce and eliminate the pathogenic effect of thrombogenic and inflammation-relevant factors. The NHE inhibitors of the present invention can therefore be combined with further anticoagulant and/or thrombolytic active ingredients such as, for example, recombinant or natural tissue plasminogen activator, streptokinase, urokinase, acetylsalicylic acid, thrombin antagonists, factor Xa antagonists, drugs with fibrinolytic activity, thromboxane receptor antagonists, phosphodiesterase inhibitors, factor VIIa antagonists, clopidogrel, ticlopidine etc. Combined use of the present NHE inhibitors with NCBE inhibitors and/or with inhibitors of carbonic anhydratase such as, for example, with acetazolamide is particularly beneficial.

The NHE inhibitors of the invention are additionally notable for a strong inhibitory effect on the proliferation of cells, for example fibroblast cell proliferation and the proliferation of smooth vascular muscle cells. The compounds of the formula I are therefore suitable as valuable therapeutic agents for diseases in which cell proliferation represents a primary or secondary cause, and can therefore be used as antiatherosclerotics, agents against chronic renal failure, cancers. They can thus be used for the treatment of organ hypertrophies and hyperplasias, for example of the heart and of the prostate. Compounds of the formula I are therefore suitable for the prevention and treatment of heart failure (congestive heart failure =CHF) and for the treatment and prevention of prostate hyperplasia or prostate hypertrophy.

NHE inhibitors are further notable for a retardation or prevention of fibrotic disorders. They are thus suitable as outstanding agents for the treatment of fibroses of the heart, and of pulmonary fibrosis, hepatic fibrosis, renal fibrosis and other fibrotic disorders.

Since NHE is significantly elevated in essential hypertensives, the compounds of the formula I are suitable for the prevention and treatment of high blood pressure and of cardiovascular disorders. They can be used in this connection alone or with a suitable combination partner for the treatment of high blood pressure and for the treatment of cardiovascular disorders. Thus, for example, one or more diuretics having a thiazide-like action, loop diuretics, aldosterone and pseudoaldosterone antagonists such as hydrochlorothiazide, indapamide, polythiazide, furosemide, piretanide, torasemide, bumetamide, amiloride, triamteren, spironolactone or eplernone, can be combined with compounds of the formula I. The NHE inhibitors of the present invention can moreover be used in combination with calcium antagonists such as verapamil, diltiazem, amlodipine or nifedipine, and with ACE inhibitors such as, for example, ramipril, enalapril, lisinopril, fosinopril or captopril. Further beneficial combination partners are also β blockers such as metoprolol, albuterol etc., antagonists of the angiotensin receptor and its receptor subtypes such as losartan, irbesartan, valsartan, omapatrilat, gernopatrilat, endothelin antagonists, renin inhibitors, adenosine receptor agonists, inhibitors and activators of potassium channels such as glibenclamide, glimepiride, diazoxide, cromokalim, minoxidil and derivatives thereof, activators of the mitochondrial ATP-sensitive potassium channel (mitoK(ATP) channel), inhibitors of further potassium channels such as of Kv1.5 etc.

As a result of their antiinflammatory effect, NHE inhibitors of the invention can be used as antiinflammatory drugs. Mechanistically notable in this connection is the inhibition of the release of mediators of inflammation. The compounds can thus be used alone or in combination with an antiinflammatory drug for the prevention or treatment of chronic and acute inflammatory disorders. Combination partners which are advantageously used are steroidal and non-steroidal antiinflammatory drugs.

It has additionally been found that NHE inhibitors show a beneficial effect on serum lipoproteins. They can therefore be used for the prophylaxis and regression of atherosclerotic lesions by eliminating a causal risk factor. These include not only the primary hyperlipidemias, but also certain secondary hyperlipidemias like those occurring for example in association with diabetes. In addition, NHE inhibitors lead to a marked reduction in the infarctions induced by metabolic abnormalities and in particular to a significant reduction in the induced infarct size and its severity. NHE inhibitors of the formula I are therefore advantageously used for the manufacture of a medicament for the treatment of hypercholesterolemia; for the manufacture of a medicament for the prevention of atherogenesis; for the manufacture of a medicament for the prevention and treatment of atherosclerosis, for the manufacture of a medicament for the prevention and treatment of diseases induced by elevated cholesterol levels, for the manufacture of a medicament for the prevention and treatment of diseases induced by endothelial dysfunction, for the manufacture of a medicament for the prevention and treatment of atherosclerosis-induced hypertension, for the manufacture of a medicament for the prevention and treatment of atherosclerosis-induced thromboses, for the manufacture of a medicament for the prevention and treatment of ischemic damage induced by hypercholesterolemia and endothelial dysfunction, and postischemic reperfusion damage, for the manufacture of a medicament for the prevention and treatment of cardiac hypertrophies and cardiomyopathies and of congestive heart failure (CHF), for the manufacture of a medicament for the prevention and treatment of coronary vasospasms and myocardial infarction induced by hypercholesterolemia and endothelial dysfunction, for the manufacture of a medicament for the treatment of said disorders in combinations with hypotensive substances, preferably with angiotension converting enzyme (ACE) inhibitors and angiotensin receptor antagonists. Combination of an NHE inhibitor of the formula I with an active ingredient which lowers the blood lipid level, preferably with an HMG-CoA reductase inhibitor (e.g. lovastatin or pravastatin), where the latter brings about a hypolipidemic effect and thus increases the hypolipidemic properties of the NHE inhibitor of the formula I, represents a favorable combination with enhanced effect and reduced use of active ingredient.

Thus, NHE inhibitors lead to effective protection from endothelial damage of various origins. With this protection of vessels against the syndrome of endothelial dysfunction, NHE inhibitors are valuable pharmaceuticals for the prevention and treatment of coronary vasospasms, peripheral vascular diseases, especially intermittent claudication, atherogenesis and atherosclerosis, left-ventricular hypertrophy and dilated cardiomyopathy, and thrombotic disorders.

NHE inhibitors are additionally suitable for the treatment of non-insulin-dependent diabetes (NIDDM), in which case for example insulin resistance is restrained. It may in this connection be beneficial, for enhancing the anti-diabetic efficacy and quality of the effect of the compounds of the invention, to combine them with a biguanide such as metformin, with an anti-diabetic sulfonylurea such as glyburide, glimepiride, tolbutamide etc., with a glucosidase inhibitor, with a peroxisome proliferator agonist receptor (PPAR) agonist such as rosiglitazone, pioglitazone etc., with an insulin product of different administration form, with a DB4 inhibitor, with an insulin sensitizer or with meglitinide.

Besides the acute anti-diabetic effects, NHE inhibitors counteract the development of late complications of diabetes and can therefore be used as pharmaceuticals for the prevention and treatment of late damage from diabetes, such as diabetic nephropathy, diabetic neuropathy, diabetic retinopathy, diabetic cardiomyopathy and other disorders arising as a consequence of diabetes. They can in this connection be advantageously combined with the antidiabetic pharmaceuticals described above under NIDDM treatment. Combination with a beneficial dosage form of insulin may be particularly important in this connection.

NHE inhibitors show, besides the protective effects against acute ischemic events and the subsequent equally acutely stressing reperfusion events, also direct therapeutically utilizable effects against disorders and impairments of the whole mammalian organism which are associated with the manifestations of the chronically progressive aging process and which are also independent of acute states of defective blood supply and may also occur under normal, non-ischemic conditions. These pathological, age-related manifestations induced over the long aging period, such as disease, invalidity and death, which can now be made amenable to treatment with NHE inhibitors, are disorders and impairments which are essentially caused by age-related changes in vital organs and the function thereof and become increasingly important in the aging organism.

Disorders associated with an age-related functional impairment, with age-related manifestations of wear of organs, are, for example, the inadequate response and reactivity of the blood vessels to contraction and relaxation reactions. This age-related decline in the reactivity of vessels to constricting and relaxing stimuli, which are an essential process of the cardiovascular system and thus of life and health, can be significantly eliminated or reduced by NHE inhibitors. An important function and a measure of the maintenance of the reactivity of vessels is the blockade or retardation of the age-related progression of endothelial dysfunction, which can be eliminated highly significantly by NHE inhibitors. NHE inhibitors are thus outstandingly suitable for the treatment and prevention of the age-related progression of endothelial dysfunction, in particular of intermittent claudication. NHE inhibitors are thus outstandingly suitable in addition for the treatment and prevention of heart failure, of congestive heart failure (CHF) and for the treatment and in particular for the prevention of age-related types of cancer.

Combination with hypotensive medicaments such as with ACE inhibitors, angiotensin receptor antagonists, diuretics, $Ca^{2+}$ antagonists etc. or with metabolism-normalizing medicaments such as cholesterol-lowering agents comes into consideration in this connection. The compounds of the formula I are thus suitable for the prevention of age-related tissue changes and for maintaining health and prolonging life while maintaining a high quality of life.

The compounds of the invention are effective inhibitors of the cellular sodium-proton antiporter (Na/H exchanger) which in a large number of disorders (essential hypertension, atherosclerosis, diabetes etc.) is also elevated in cells which are easily amenable to measurements, such as, for example, in erythrocytes, platelets or leukocytes. The compounds used according to the invention are therefore suitable as excellent and simple scientific tools, for example in their use as diagnostic aids for diagnosing and distinguishing particular types of hypertension, but also of atherosclerosis, of diabetes and the late complications of diabetes, proliferative disorders etc.

NHE inhibitors are further suitable for the treatment of diseases (human and veterinary) induced by bacteria and by protozoa. In the context of diseases caused by protozoa, particular mention should be made of malarial diseases of humans and coccidiosis of poultry.

The compounds are also suitable as agents for controlling sucking parasites in human and veterinary medicine and in crop protection. Preference is given in this connection to the use as agents against blood-sucking parasites in human and veterinary medicine.

Said compounds are therefore advantageously used alone or in combination with other pharmaceuticals or active ingredients for the manufacture of a medicament for the treatment or prophylaxis of impairments of respiratory drive, of respiratory disorders, sleep-related respiratory disorders, sleep apneas, of snoring, of acute and chronic renal disorders, of acute renal failure and of chronic renal failure, of impairments of bowel function, of high blood pressure, of essential hypertension, of central nervous system disorders, of disorders resulting from CNS overexcitability, epilepsy and centrally induced spasms or of anxiety states, depressions and psychoses, of ischemic states of the peripheral or central nervous system or of stroke, of acute and chronic damage and disorders of peripheral organs or limbs caused by ischemic or reperfusion events, of atherosclerosis, of impairments of lipid metabolism, of thromboses, of impairments of biliary function, of infestation by ectoparasites, of disorders resulting from endothelial dysfunction, of protozoal diseases, of malaria, for the preservation and storage of transplants for surgical procedures, for use in surgical operations and organ transplantations or for the treatment of states of shock or of diabetes and late damage from diabetes or of diseases in which cell proliferation represents a primary or secondary cause, and for maintaining health and prolonging life.

The invention further relates to the use of the compounds of the formula I and the pharmaceutically acceptable salts thereof for use as medicament.

The invention also relates to medicines/pharmaceutical preparations for human, veterinary or phytoprotective use comprising an effective amount of a compound of the formula I and/or of a pharmaceutically acceptable salt thereof, as well as pharmaceutical preparations for human, veterinary or phytoprotective use comprising an effective amount of a compound of the formula I and/or of a pharmaceutically acceptable salt thereof alone or in combination with one or more other pharmacological active ingredients or pharmaceuticals.

Pharmaceuticals which comprise a compound of the formula I or the pharmaceutically acceptable salts thereof can be administered for example orally, parenterally, intramuscularly, intravenously, rectally, nasally, by inhalation, subcutaneously or by a suitable transcutaneous dosage form, the preferred administration depending on the respective manifestation of the disorder. The compounds of the formula I can moreover be used alone or together with pharmaceutical excipients, specifically both in veterinary and in human medicine and in crop protection. The pharmaceuticals comprise active ingredients of the formula I and/or pharmaceutically acceptable salts thereof generally in an amount of from 0.01 mg to 1 g per dose unit.

The skilled worker is familiar on the basis of his expert knowledge with the excipients suitable for the desired pharmaceutical formulation. Besides solvents, gel formers, suppository bases, tablet excipients and other active ingredient carriers it is possible to use for example antioxidants, dispersants, emulsifiers, antifoams, masking flavors, preservatives, solubilizers or colorants.

For a form for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry and as wet granules. Examples of suitable oily carriers or solvents are vegetable or animal oils, such as sunflower oil or fish liver oil.

For subcutaneous, percutaneous or intravenous administration, the active compounds used are converted, if desired with the substances usual for this purpose, such as solubilizers, emulsifiers or further excipients, into solution, suspension or emulsion. Examples of suitable solubilizers are: water, physiological saline or alcohols, e.g. ethanol, propanol, glycerol, as well as sugar solutions such as glucose or mannitol solutions, or also a mixture of the various solvents mentioned.

Suitable as pharmaceutical formulation for administration in the form of aerosols or sprays are for example solutions, suspensions or emulsions of the active ingredient of the formula I in a pharmaceutically acceptable solvent such as, in particular, ethanol or water, or a mixture of such solvents. The formulation may, if required, also comprise other pharmaceutical excipients such as surfactants, emulsifiers and stabilizers, and a propellant gas. Such a preparation normally comprises the active ingredient in a concentration of about 0.1 to 10, in particular of about 0.3 to 3% by weight.

The dosage of the active ingredient of the formula I to be administered and the frequency of administration depend on the potency and duration of action of the compounds used; additionally also on the nature and severity of the disease to be treated and on the gender, age, weight and individual response of the mammal to be treated.

On average, the daily dose of a compound of the formula I for a patient weighing about 75 kg is at least 0.001 mg/kg, preferably 0.1 mg/kg, to a maximum of 30 mg/kg, preferably 1 mg/kg, of body weight. In acute situations, for example immediately after suffering apneic states at high altitude, higher doses may also be necessary. Up to 300 mg/kg per day may be necessary in particular on i.v. administration, for example for an infarct patient in intensive care. The daily dose can be divided into one or more, for example up to 4, single doses.

DESCRIPTIONS OF EXPERIMENTS AND EXAMPLES

List of abbreviations used:

m.p. melting point

MPRC Cartridge L-026-30; Sl60 40-63 µm; Super Vario Flash; max. press. 3 bar Götec-Labortechnik GmbH MPLC medium pressure liquid chromatography THF tetrahydrofuran RT room temperature Example 1

1-Amino-4-(4-aminophenyl)-6-chloro-3,4-dihydroisoquinoline Hydrochloride (1A) and 1-amino-4-(4-aminophenyl)-3,4-dihydroisoquinoline Hydrochloride (1B)

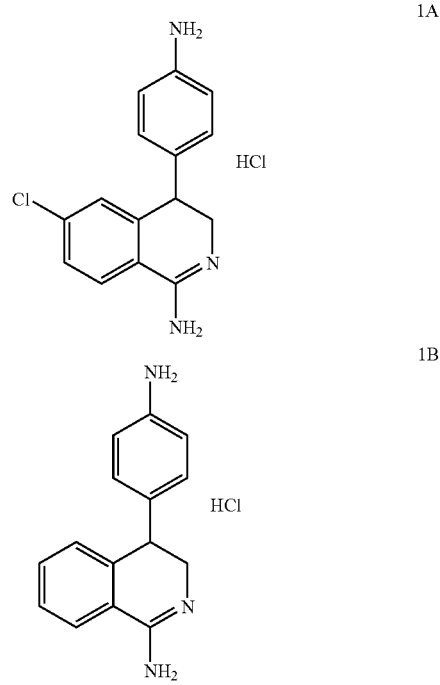

a) 3'-Chloro-4-nitrodiphenylacetonitrile

A mixture of 3 g of 3-chlorobenzyl cyanide, 3.1 g of 1-chloro-4-nitrobenzene and 4.3 g of N-benzyl-N,N,N-triethylammonium chloride in 5 ml of THF was stirred at room temperature for about 10 min and then a solution of 10.1 ml of 50% strength aqueous NaOH solution was added dropwise. The bluish-green solution was stirred at 60° C. for 3 hours, diluted with a little water and, after cooling to room temperature, acidified with 36% strength concentrated hydrochloric acid. Extraction with ethyl acetate and washing the organic phase with water were followed by removal of the solvent by distillation. Subsequent medium pressure liquid chromatography (MPLC) in an MPRC column with a mixture of ethyl acetate and n-heptane (2:1) isolated the oily amorphous product.

b) 2-(3-Chlorophenyl)-2-(4-nitrophenyl)ethylamine

A solution of 13.17 mmol of 3'-chloro-4-nitrodiphenylacetonitrile in anhydrous THF was added dropwise to 15.8 mmol (15.8 ml) of borane-tetrahydrofuran complex. After stirring at room temperature for 4 hours and leaving to stand at RT for a further 15 hours, the solvent was removed by distillation under reduced pressure in a Rotavapor, ethanol and a few drops of 36% strength concentrated hydrochloric acid were added to the residue and, after heating on a steam bath for about 30 minutes, the ethanolic solvent was removed by distillation. The green oily residue was mixed with water, made alkaline with 2N NaOH, extracted with ethyl acetate and, after washing the organic phase, dried and the solvent was removed by distillation in a Rotavapor. MPLC column chromatography with an MPRC and a mixture of dichloromethane and methanol (10:1) resulted in the desired product as greenish amorphous oil.

c) 2-(3-Chlorophenyl)-2-(4-nitrophenyl)ethyl Isothiocyanate

A solution of 1.192 mmol of thiophosgene in 5 ml of methylene chloride was added to an aqueous solution of 2.71 mmol of sodium bicarbonate. Then, over the course of 15 minutes, a mixture of 1.084 mmol of 2-(3-chlorophenyl)-2-(4-nitrophenyl)ethylamine was added dropwise to this mixture. After removal of the organic phase and extraction of the aqueous phase once again with dichloromethane, the combined organic phases were washed with water and the solvent was removed by distillation under reduced pressure in a Rotavapor. The reddish oily 2-(3-chlorophenyl)-2-(4-nitrophenyl)ethyl isothiocyanate was stored in a closed vessel with exclusion of moisture in a refrigerator until processed further.

d) 6-Chloro-1-mercapto-4-(4-nitrophenyl)-3,4-dihydroisoquinoline 1.75 ml of concentrated sulfuric acid were added to 0.4 g (1.255 mmol) of 2-(3-chlorophenyl)-2-(4-nitrophenyl)ethyl isothiocyanate with external ice cooling and internal stirring. Stirring at RT for a further 4 hours was followed by addition of ice-water and extraction with dichloromethane.

e) 6-Chloro-1-methylthio-4-(4-nitrophenyl)-3,4-dihydroisoquinoline

Reaction of 0.48 g of 6-chloro-1-mercapto-4-(4-nitrophenyl)-3,4-dihydroisoquinoline in 20 ml of acetone with 0.85 g of methyl iodide for 3 hours and subsequent removal of the acetone by distillation resulted in 6-chloro-1-methylthio-4-(4-nitrophenyl)-3,4-dihydroisoquinoline hydroiodide as a yellow solid.

m.p.: 177-182° C.

The corresponding free base 6-chloro-1-methylthio-4-(4-nitrophenyl)-3,4-dihydroisoquinoline could be liberated from the hydroiodide with aqueous 2N NaOH and extracted with ethyl acetate. Partly solid product.

f) 1-Amino-6-chloro-4-(4-nitrophenyl)-3,4-dihydroisoquinoline

A solution of 0.45 g of 6-chloro-1-methylthio-4-(4-nitrophenyl)-3,4-dihydroisoquinoline and 30 ml of ammonia-saturated THF solution was heated in an autoclave at 80° C. for 10 hours and then at 12° C. for a further 15 hours. Subsequent MPLC on an MPRC cartridge and a mixture of 20 parts by volume of ethyl acetate:10 parts by volume of n-heptane:3 parts by volume of glacial acetic acid leads to elution of starting material (6-chloro-1-methylthio-4-(4-nitrophenyl)-3,4-dihydroisoquinoline). Subsequent elution with methanol results in 1-amino-6-chloro-4-(4-nitrophenyl)-3,4-dihydroisoquinoline.

m.p.: 170-185° C.

g) 1-Amino-4-(4-aminophenyl)-6-chloro-3,4-dihydroisoquinoline Hydrochloride (1A) and 1-amino-4-(4-aminophenyl)-3,4-dihydroisoquinoline Hydrochloride (1B)

A mixture of 210 mg of 1-amino-6-chloro-4-(4-nitrophenyl)-3,4-dihydroisoquinoline, 10 ml of ethanol, 1 ml of concentrated hydrochloric acid (36%) and 87 mg of platinum(IV) oxide were hydrogenated at room temperature under atmospheric pressure until hydrogen uptake ceased. After removal of the solvent with distillation, 2 components were separated by MPLC on an MPRC cartridge and with a mixture of 10 parts by volume of ethyl acetate, 5 parts by volume of methanol, 5 parts by volume of n-heptane, 5 parts by volume of dichloromethane and 1 part by volume of ammonia (concentrated).

The product was dissolved in a little ethyl acetate, acidified with ethereal HCl, stirred at room temperature and filtered with suction. 1-Amino-4-(4-aminophenyl)-6-chloro-3,4-dihydroisoquinoline hydrochloride (1A) was obtained as a colorless crystalline substance.

Rf=0.16 (silica gel, ethyl acetate/methanol/heptane/dichloromethane/ammonia 10:5:5:5:1)

m.p.: 278-284° C.

MS m/z=271 (m)+

The product was also dissolved in a little ethyl acetate, acidified with ethereal HCl, stirred at room temperature and filtered with suction. 1-Amino-4-(4-aminophenyl)-3,4-dihydroisoquinoline hydrochloride (1B) was obtained as a colorless crystalline substance.

Rf=0.11 (silica gel, ethyl acetate/methanol/heptane/dichloromethane/ammonia 10:5:5:5:1)

MS m/z=237 (m)+

Example 2

1-Amino-4-(2-aminophenyl)-6-chloro-3,4-dihydroisoquinoline Hydrochloride

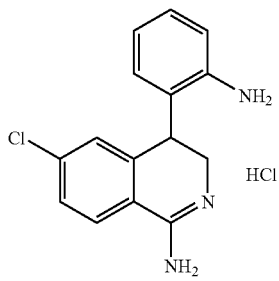

a) 3'-Chloro-2-nitrodiphenylacetonitrile was obtained in analogy to the method indicated in Example 1a) from 3-chlorobenzyl cyanide, 2-fluoronitrobenzene in the presence of N-benzyl-N,N,N-triethylammonium chloride as two-phase catalyst as oily amorphous product.

b) 2-(3-Chlorophenyl)-2-(2-nitrophenyl)ethylamine Acetate was obtained in analogy to the method indicated in Example 1b) by selective reduction of the nitrile group with $BH_3$ THF complex.

c) 2-(3-Chlorophenyl)-2-(2-nitrophenyl)ethyl Isothiocyanate was obtained in analogy to the method indicated in Example 1c) from 2-(3-chlorophenyl)-2-(2-nitrophenyl)ethylamine acetate and thiophosgene in dichloromethane and analogous storage under inert gas in a refrigerator until reacted further.

d) 6-Chloro-1-mercapto-4-(2-nitrophenyl)-3,4-dihydroisoquinoline was obtained in analogy to the method indicated in Example 1d) from 2-(3-chlorophenyl)-2-(2-nitrophenyl)ethylisothiocyanate and concentrated sulfuric acid as amorphous semisolid product.

e) 6-Chloro-1-methylthio-4-(2-nitrophenyl)-3,4-dihydroisoquinoline was obtained in analogy to the method indicated in Example 1e) from 6-chloro-1-mercapto-4-(2-nitrophenyl)-3,4-dihydroisoquinoline and methyl iodide and subsequent treatment with 2N sodium hydroxide solution. Yellow amorphous oil.

f) 1-Amino-6-chloro-4-(2-nitrophenyl)-3,4-dihydroisoquinoline Hydrochloride was obtained in analogy to the method indicated in Example 1f) from 6-chloro-1-methylthio-4-(2-nitrophenyl)-3,4-dihydroisoquinoline as amorphous product which was reacted further in stage g) without further purification operations.

g) 1-Amino-4-(2-aminophenyl)-6-chloro-3,4-dihydroisoquinoline Hydrochloride was obtained in analogy to the method indicated in Example 1 g) from 1-amino-6-chloro-4-(2-nitrophenyl)-3,4-dihydroisoquinoline hydrochloride by hydrogenation with $PtO_2$ and MPLC and an elution mixture of 10 parts by volume of ethyl acetate, 5 parts by volume of n-heptane, 5 parts by volume of dichloromethane, 5 parts by volume of methanol and 1 part by volume of concentrated aqueous ammonia solution. The product was dissolved in a little ethyl acetate, acidified with ethereal HCl, stirred at room temperature and filtered off with suction.

Decomposition point above 175° C. (foaming).

Example 3

4-(4-Aminophenyl)-6-chloro-1-methylamino-3,4-dihydroisoquinoline Hydrochloride

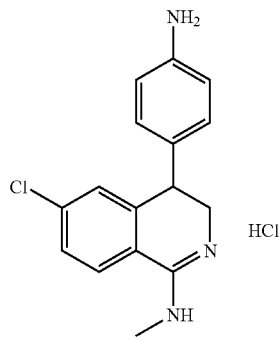

a) 6-Chloro-1-methylamino-4-(4-nitrophenyl)-3,4-dihydroisoquinoline 400 mg of 6-chloro-1-methylthio-4-(4-nitrophenyl)-3,4-dihydroisoquinoline (see compound 1e) were heated with 2 g of methylamine in THF at 120° C. in a shaking autoclave under inert gas for 20 hours. Removal of the solvent by distillation was followed by MPLC chromatography on an MPRC cartridge with a mixture of 10 parts by volume of ethyl acetate, 5 parts by volume of n-heptane, 5 parts by volume of dichloromethane, 5 parts by volume of methanol and 1 part by volume of concentrated aqueous ammonia solution.

Solid, m.p.: 60-65° C. (amorphous product)

b) 6-Chloro-1-methylamino-4-(4-nitrophenyl)-3,4-dihydroisoquinoline Hydrochloride was obtained by leaving an ethyl acetate solution of 15 mg of 6-chloro-1-methylamino-4-(4-nitrophenyl)-3,4-dihydroisoquinoline to stand after adding a saturated solution of hydrogen chloride gas in diethyl ether. 6-Chloro-1-methylamino-4-(4-nitrophenyl)-3,4-dihydroisoquinoline hydrochloride crystallized from the solution as colorless crystalline product after brief heating and was filtered off.

m.p.: 282-285° C.

c) 4-(4-Aminophenyl)-6-chloro-1-methylamino-3,4-dihydroisoquinoline 135.2 mg of iron powder were added to a solution of 255 mg of 6-chloro-1-methylamino-4-(4-nitrophenyl)-3,4-dihydroisoquinoline in 4.5-5 ml of glacial acetic acid and then 1.8 ml of concentrated hydrochloric acid were added dropwise, and the mixture was boiled under reflux conditions for 2 hours. The solvent was removed by distillation, and the residue was mixed with water and made alkaline with 2N NaOH. This aqueous phase was extracted with ethyl acetate and purified by MPLC chromatography using an MPRC cartridge with a mixture of 10 parts by volume of ethyl acetate, 5 parts by volume of n-heptane, 5 parts by volume of dichloromethane, 5 parts by volume of methanol and 1 part by volume of concentrated aqueous ammonia solution. Amorphous product.

d) 4-(4-Aminophenyl)-6-chloro-1-methylamino-3,4-dihydroisoquinoline Hydrochloride was obtained in analogy to the method indicated in Example 3b from an ethyl acetate solution of 4-(4-aminophenyl)-6-chloro-1-methylamino-3,4-dihydroisoquinoline with ethereal hydrogen chloride solution. Colorless crystalline substance.

m.p.: 306-310° C.

Example 4

4-(4-Aminophenyl)-6-chloro-1-dimethylamino-3,4-dihydroisoquinoline Hydrochloride

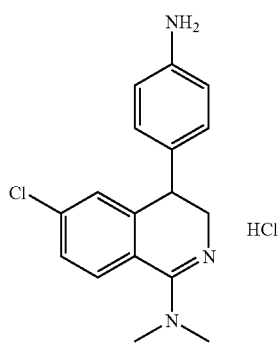

a) 6-Chloro-1-dimethylamino-4-(4-nitrophenyl)-3,4-dihydroisoquinoline 400 mg of 6-chloro-1-methylthio-4-(4-nitrophenyl)-3,4-dihydroisoquinoline (compound 1) were heated with 20 ml of dimethylamine in THF at 120° C. in a shaking autoclave under inert gas for 20 hours. Removal of the solvent by distillation was followed by MPLC chromatography on an MPRC cartridge with a mixture of 10 parts by volume of ethyl acetate, 5 parts by volume of n-heptane, 5 parts by volume of dichloromethane, 5 parts by volume of methanol and 1 part by volume of concentrated aqueous ammonia solution. Semisolid, partly amorphous product.

b) 4-(4-Aminophenyl)-6-chloro-1-dimethylamino-3,4-dihydroisoquinoline Hydrochloride 100 mg of iron powder were added to a solution of 195 mg of 6-chloro-1-dimethylamino-4-(4-nitrophenyl)-3,4-dihydroisoquinoline in 3.5 ml of glacial acetic acid and then 1.8 ml of concentrated hydrochloric acid were added dropwise, and the mixture was boiled under reflux conditions for 2 hours. The solvent was removed by distillation, and the residue was mixed with water and made alkaline with 2N NaOH. This aqueous phase was extracted with ethyl acetate and purified by MPLC chromatography using an MPRC cartridge with a mixture of 10 parts by volume of ethyl acetate, 5 parts by volume of n-heptane, 5 parts by volume of dichloromethane, 5 parts by volume of methanol and 1 part by volume of concentrated aqueous ammonia solution. After removal of the solvent in a Rotavapor, the viscous amorphous residue was treated in ethyl acetate with ethereal hydrogen chloride solution, and the crystalline solid was filtered off.

m.p.: 255-260° C.

Example 5

4-(4-Aminophenyl)-6-chloro-1-(N-pyrrolidino)-3,4-dihydroisoquinoline Hydrochloride

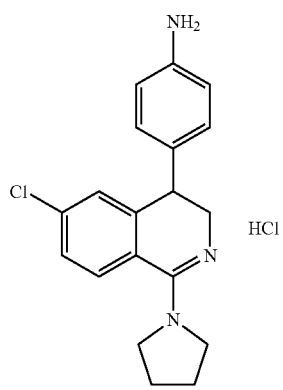

a) 6-Chloro-4-(4-nitrophenyl)-1-(N-pyrrolidino)-3,4-dihydroisoquinoline 300 mg of 6-chloro-1-methylthio-4-(4-nitrophenyl)-3,4-dihydroisoquinoline (compound 1) were heated with 0.151 ml of pyrrolidine at 120° C. for 3 hours. Removal of the solvent by distillation was followed by MPLC chromatography on an MPRC cartridge with a mixture of equal parts by volume of dichloromethane and methanol. Semisolid, partly crystalline product.

b) 4-(4-Aminophenyl)-6-chloro-1-(N-pyrrolidino)-3,4-dihydroisoquinoline 80.6 mg of iron powder were added to a solution of 171.2 mg of 6-chloro-1-(N-pyrrolidino)-4-(4-nitrophenyl)-3,4-dihydroisoquinoline in 2.8 ml of glacial acetic acid and then 1.8 ml of concentrated hydrochloric acid were added dropwise, and the mixture was boiled under reflux conditions for 2 hours. The solvent was removed by distillation, the residue was mixed with water and made alkaline with 2N NaOH. This aqueous phase was extracted with ethyl acetate and purified by MPLC chromatography using an MPRC cartridge with a mixture of 10 parts by volume of ethyl acetate, 5 parts by volume of n-heptane, 5 parts by volume of dichloromethane, 5 parts by volume of methanol and 1 part by volume of concentrated aqueous ammonia solution. Partly amorphous product.

c) 4-(4-Aminophenyl)-6-chloro-1-(N-pyrrolidino)-3,4-dihydroisoquinoline Hydrochloride was obtained in analogy to the method indicated in Example 3b from an ethyl acetate solution of 4-(4-aminophenyl)-6-chloro-1-(N-pyrrolidino)-3,4-dihydroisoquinoline with ethereal hydrogen chloride solution. Colorless crystalline substance. Melting with decomposition above 250° C.

Example 6

N-(Ethoxycarbonylmethyl)-N'-4-[(6-chloro-3,4-dihydro-1-dimethylaminoisoquinolin-4-yl)phenyl]urea Hydrochloride

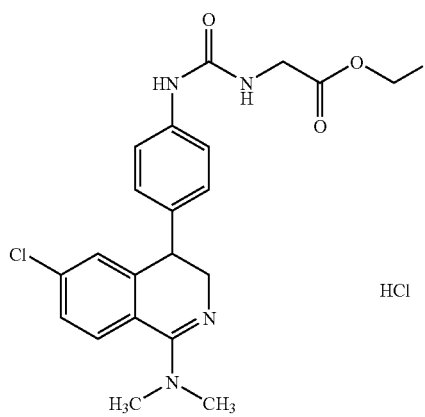

a) 6-Chloro-1-dimethylamino-4-(4-nitrophenyl)-3,4-dihydroquinoline 400 mg of 6-chloro-1-methylthio-4-(4-nitrophenyl)-3,4-dihydroisoquinoline (compound 1) were heated with a 2M solution of THF/dimethylamine (20 ml) in a shaking autoclave at 120° C. for 20 hours. Removal of the solvent by distillation was followed by MPLC chromatography on an MPRC cartridge with a mixture of equal parts by volume of dichloromethane and methanol. A semicrystalline solid was obtained.

b) 4-(4-Aminophenyl)-6-chloro-1(dimethylamino)-3,4-dihydroisoquinoline 99 mg of iron powder were added to a solution of 195 mg of 6-chloro-1-dimethylamino-4-(4-nitrophenyl)-3,4-dihydroquinoline in 3 ml of glacial acetic acid and then 1.8 ml of concentrated hydrochloric acid were added dropwise, and the mixture was boiled under reflux conditions for 2 hours. The solvent was removed by distillation, the residue was mixed with water and made alkaline with 2N NaOH. This aqueous phase was extracted with ethyl acetate and purified by MPLC chromatography using an MPRC cartridge with a mixture of 10 parts by volume of ethyl acetate, 5 parts by volume of n-heptane, 5 parts by volume of dichloromethane, 5 parts by volume of methanol and 1 part by volume of concentrated aqueous ammonia solution. The resulting viscous residue is suspended in ethyl acetate and acidified with ether/HCl. The crystalline solid was filtered off.

Melting with decomposition above 250° C.

c) N-(Ethoxycarbonylmethyl)-N'-4-[(6-chloro-3,4-dihydro-1-dimethylaminoisoquinolin-4-yl)phenyl] urea Reaction of 76 mg of 4-(4-aminophenyl)-6-chloro-1 (dimethylamino)-3,4-dihydroisoquinoline in 6 ml of dichloromethane with 33 mg of ethyl isocyanatoacetate in 3 ml of dichloromethane for 3 hours and subsequent removal of the dichloromethane by distillation resulted in N-(ethoxycarbonylmethyl)-N'-4-[(6-chloro-3,4-dihydro-1-dimethylaminoisoquinolin-4-yl)phenyl]urea as dark yellow solid residue. Subsequent MPLC on an MPRC cartridge with a mixture of 10 part by volume of ethyl acetate, 5 part by volume of n-heptane, 5 part by volume of dichloromethane, 5 part by volume of methanol and 1 part by volume of concentrated aqueous ammonia solution led to elution of product. The product was mixed with a little ethyl acetate and acidified with ethereal HCl.

m.p.: 120° C.

Example 7

3-{4-[(6-Chloro-3,4-dihydro-1-dimethylaminoisoquinolin-4-yl)phenyl]}-imidazolidine-2,4-dione Hydrochloride

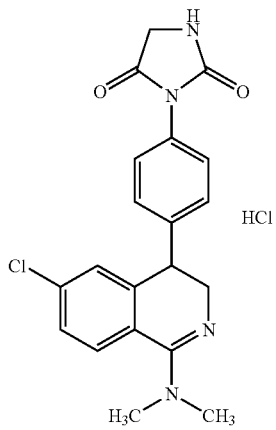

43 mg of N-(ethoxycarbonylmethyl)-N'-4-[(6-chloro-3,4-dihydro-1-dimethylamino-isoquinolin-4-yl)phenyl]urea (Example 6) were boiled under reflux in 5 ml of 6N HCl for 6 hours. After stirring at room temperature for 1 hour, the water was removed by distillation. The residue was mixed with a little water and neutralized with saturated $K_2CO_3$ solution. A solid precipitates out and was purified by MPLC chromatography using an MPRC cartridge with a mixture of 10 part by volume of ethyl acetate, 5 part by volume of n-heptane, 5 part by volume of dichloromethane, 6 part by volume of methanol and 1 part by volume of concentrated aqueous ammonia solution. The product was dissolved in a little ethyl acetate, acidified with ethereal HCl, stirred at room temperature and filtered off with suction.

m.p.: above 140° C., sublimation beginning >310° C.

Pharmacological Data:

Description of Assay: Determination of the NHE-Inhibitory Effect

In this assay, the recovery of the intracellular pH ($pH_i$) after an acidification which occurs even under bicarbonate-free conditions with functional NHE was determined. To this end, the $pH_i$ was determined using the pH-sensitive fluorescent dye BCECF (Calbiochem, the precursor BCECF-AM was employed). The cells were initially loaded with BCECF. The BCECF fluorescence was determined in a ratio fluorescence spectrometer (Photon Technology International, South Brunswick, N.J., USA) with excitation wavelengths of 505 and 440 nm and an emission wavelength of 535 nm and converted into the $pH_j$ using calibration plots. The cells had been incubated in $NH_4Cl$ buffer (pH 7.4) for the BCECF loading ($NH_4Cl$ buffer: 115 mM NaCl, 20 mM $NH_4Cl$, 5 mM KCl, 1 mM $CaCl_2$, 1 mM $MgSO_4$, 20 mM Hepes, 5 mM glucose, 1 mg/ml BSA; a pH of 7.4 was adjusted with 1 M NaOH). The intracellular acidification was induced by adding 975 µl of an $NH_4Cl$-free buffer (see below) to 25 µl aliquots of the cells incubated in $NH_4Cl$ buffer. The subsequent rate of pH recovery was recorded for two minutes with NHE1, five minutes with NHE2 and three minutes with NHE3. To calculate the inhibitory power of the tested substances, the cells were initially investigated in buffers with which there was complete or absolutely no pH recovery. For complete pH recovery (100%), the cells were incubated in $Na^+$-containing buffer (133.8 mM NaCl, 4.7 mM KCl, 1.25 mM $CaCl_2$, 1.25 mM $MgCl_2$, 0.97 mM $Na_2HPO_4$, 0.23 mM $NaH_2PO_4$, 5 mM Hepes, 5 mM glucose, a pH of 7.0 was adjusted with 1 M NaOH). To determine the 0% value, the cells were incubated in an $Na^+$-free buffer (133.8 mM choline chloride, 4.7 mM KCl, 1.25 mM $CaCl_2$, 1.25 mM $MgCl_2$, 0.97 mM $K_2HPO_4$, 0.23 mM $KH_2PO_4$, 5 mM Hepes, 5 mM glucose, a pH of 7.0 was adjusted with 1 M NaOH). The substances to be tested were made up in the $Na^+$-containing buffer. The recovery of the intracellular pH at each tested concentration of a substance was expressed as a percentage of the maximum recovery. The $IC_{50}$ of the respective substance for the individual NHE subtypes was calculated from the percentages of pH recovery using the Sigma Plot program.

The inhibitory effect ($IC_{50}$ values) on NHE3 by various exemplary compounds is detailed in the table below:

| Example | $IC_{50}$ [µM] |
|---|---|
| 1A | 1.95 |
| 1B | 8.24 |
| 2 | 1.63 |
| 3 | 4.93 |
| 4 | 10 |
| 5 | 10 |
| 6 | 10 |

What is claimed is:
1. A compound of formula I

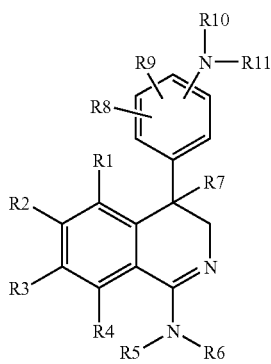

wherein:
R1, R2, R3 and R4 are independently selected from the group consisting of hydrogen, F, Cl, Br, I, CN, $NO_2$, $CF_3$, $CH_3$—$SO_2$, alkyl having 1, 2, 3 or 4 carbon (C) atoms, $NH_2$, NH—$CH_3$ and N($CH_3$)$_2$;

R5 and R6 are independently selected from the group consisting of hydrogen, alkyl having 1, 2, 3, 4, 5 or 6 C atoms, $CF_3$—$CH_2$—, cycloalkyl having 3, 4, 5 or 6 C atoms and cyclopropyl-$CH_2$—,
or
R5 and R6, together with the nitrogen atom to which they are bonded form a 4-, 5-, 6-, 7-, 8-, 9- or 10-membered ring in which one or two $CH_2$ groups may be replaced independently of one another by NR12, sulfur, oxygen, C(O) or $SO_2$;
R12 is a hydrogen, alkyl having 1, 2, 3 or 4 C atoms or cycloalkyl having 3, 4, 5 or 6 C atoms;
R7 is a hydrogen or alkyl group having 1, 2, 3 or 4 C atoms;
R8 and R9 are independently selected from the group consisting of hydrogen, F, Cl, Br, OH, an alkyl group having 1, 2, 3 or 4 C atoms, $CH_3O$, $CF_3$, and $CH_3SO_2$;
R10 and 11 are R13-($C_mH_{2m}$)—$B_n$, where
m zero, 1, 2, 3 or 4;
n zero or 1;
B —CO—, —CONR14- or —$SO_2$—; and
R14 is a hydrogen or an alkyl group having 1, 2, 3, 4, 5 or 6 C atoms;
R13 is selected from the group consisting of hydrogen, alkyl having 1, 2, 3 or 4 C atoms, cycloalkyl having 3, 4, 5 or 6 C atoms, 1-pyrrolidinyl, 1-piperidinyl, 1-(4-methylpiperazinyl), 1-morpholinyl, —COOR15, OR16, NR17R18 and phenyl each of which have at least one additional substituent selected from the group consisting of chlorine, fluorine, methyl and methoxy;
R15, R16, R17 and R18 are hydrogen or alkyl having 1, 2, 3, 4, 5 or 6 C atoms;
or
R10 and R11, together with the nitrogen atom to which they are bonded, form a 4-, 5-, 6-, 7-, 8-, 9- or 10-membered ring in which one, two, three or four $CH_2$ groups may be replaced independently of one another by NR19, sulfur, oxygen, C(O) or $SO_2$;
R19 is hydrogen, alkyl having 1, 2, 3 or 4 C atoms or cycloalkyl having 3, 4, 5 or 6 C atoms;
or a pharmaceutically acceptable salt or trifluoroacetate thereof.
2. The compound of formula I as recited in claim 1 wherein:
R1, R2, R3 and R4 are independently selected from the group consisting of hydrogen, F, Cl, Br, CN, $CF_3$, $CH_3$—$SO_2$, alkyl having 1, 2, 3 or 4 C atoms, $NH_2$, NH—$CH_3$ and N($CH_3$)$_2$;
R5 and R6 are independently selected from the group consisting of hydrogen, alkyl having 1, 2, 3, 4, 5 or 6 C atoms, $CF_3$—$CH_2$—, cycloalkyl having 3, 4, 5 or 6 C atoms and cyclopropyl-$CH_2$—,
or
R5 and R6, together with the nitrogen atom to which they are bonded form a 4-, 5-, 6-, 7-, 8-, 9- or 10-membered ring;
R7 is a hydrogen or a methyl group;
R8 and R9 are independently selected from the group consisting of hydrogen, F, Cl, OH, alkyl having 1, 2, 3 or 4 C atoms, $CH_3O$, $CF_3$, and $CH_3SO_2$;
R10 and 11 are R13-($C_mH_{2m}$)—$B_n$, where
m zero, 1, 2, 3 or 4;
n zero or 1;
B —CO—, —CONR14- or —$SO_2$—; and
R14 is a hydrogen or alkyl group having 1, 2, 3, 4, 5 or 6 C atoms;
R13 is a hydrogen or alkyl group having 1, 2, 3 or 4 C atoms, cycloalkyl having 3, 4, 5 or 6 C atoms, 1-pyrrolidinyl, 1-piperidinyl, 1-(4-methylpiperazinyl), 1-morpholinyl, —COOR15, OR16, NR17R18 or phenyl which has independently of one another 1 or 2 substituents selected from the group of chlorine, fluorine, methyl and methoxy;

R15, R16, R17 and R18 are independently hydrogen or an alkyl group having 1, 2, 3, 4, 5 or 6 C atoms;

or

R10 and R11, together with the nitrogen atom to which they are bonded, form a 4-, 5-, 6-, 7-, 8-, 9- or 10-membered ring in which one, two, three or four $CH_2$ groups may be replaced independently of one another by NR19, sulfur, oxygen, C(O) or $SO_2$; and R19 is a hydrogen or an alkyl group having 1, 2, 3 or 4 C atoms;

or a pharmaceutically acceptable salt or trifluoroacetate thereof.

3. The compound of formula I as recited in claim 2 wherein:

R1, R2, R3 and R4 are selected from the group consisting of 1-hydrogen, F, Cl, Br, CN, $CF_3$, $CH_3$—$SO_2$, methyl, ethyl, $NH_2$, NH—$CH_3$ and $N(CH_3)_2$;

R5 and R6 are independently selected from the group consisting of hydrogen, methyl, ethyl, isopropyl, $CF_3$—$CH_2$ and cycloalkyl having 3, 4, 5 and 6 C atoms;

or

R5 and R6, together with the nitrogen atom to which they are bonded, form a 4-, 5-, 6-, 7-, 8-, 9- or 10-membered ring;

R7 is a hydrogen or methyl group;

R8 and R9 are hydrogen, chlorine or methyl;

R10 and 11 are R13-($C_mH_{2m}$)—$B_n$, where m zero, 1, 2, 3 or 4;

n zero or 1;

B —CO—, —CONR14- or —$SO_2$—; and

R14 is a hydrogen or alkyl group having 1, 2, 3, 4, 5 or 6 C atoms;

R13 is a hydrogen, methyl, ethyl, isopropyl or cycloalkyl group having 3, 4, 5 or 6 C atoms, 1-pyrrolidinyl, 1-piperidinyl, 1-(4-methylpiperazinyl), —COOR15, OR16 or NR17R18; wherein R15, R16, R17 and R18 are independently hydrogen or alkyl having 1, 2, 3, 4, 5 or 6 C atoms;

or

R10 and R11, together with the nitrogen atom to which they are bonded, form a 4-, 5-, 6-, 7-, 8-, 9- or 10-membered ring, in which one, two or three —$CH_2$ groups may be replaced independently of one another by NR19, or C(O);

R19 hydrogen or methyl;

or a pharmaceutically acceptable salt or trifluoroacetate thereof.

4. The compound of formula I as recited in claim 3, wherein:

R1 and R3 are hydrogen;

R2 and R4 are hydrogen or chlorine;

R5 and R6 are hydrogen or methyl;

or

R5 and R6, together with the nitrogen atom to which they are bonded, form a 5- or 6-membered ring;

R7 is hydrogen;

R8 and R9 are hydrogen or chlorine;

R10 and 11 are R13-($C_mH_{2m}$)—$B_n$, wherein;

m is zero, 1, 2, 3 or 4;

n is zero or 1;

B is —CO— or —CONR14- and

R14 is a hydrogen or methyl;

R13 is selected from the group consisting of hydrogen, methyl, cycloalkyl having 3, 4, 5 or 6 C atoms, 1-pyrrolidinyl, 1-piperidinyl, 1-(4-methylpiperazinyl), —COOR15, OR16 or NR17R18;

R15, R16, R17 and R18 are a hydrogen or alkyl having 1, 2, 3, 4, 5 or 6 C atoms;

or

R10 and R11, together with the nitrogen atom to which they are bonded, form a 4-, 5-, 6-, 7-, 8-, 9- or 10-membered ring in which one, two or three —$CH_2$ groups may be replaced by NR19, or C(O);

R19 is hydrogen or methyl;

or a pharmaceutically acceptable salt or trifluoroacetate thereof.

5. The compound of formula I as recited in claim 4 selected from the group comprising:

1-amino-4-(4-aminophenyl)-6-chloro-3,4-dihydroisoquinoline, 1-amino-4-(4-aminophenyl)-3,4-dihydroisoquinoline, 1-amino-4-(2-aminophenyl)-6-chloro-3,4-dihydroisoquinoline, 4-(4-aminophenyl)-6-chloro-1-methylamino-3,4-dihydroisoquinoline, 4-(4-aminophenyl)-6-chloro-1-dimethylamino-3,4-dihydroisoquinoline, 4-(4-aminophenyl)-6-chloro-1-(N-pyrrolidino)-3,4-dihydroisoquinoline, N-(ethoxycarbonylmethyl)-N'-4-[(6-chloro-3,4-dihydro-1-dimethylaminoisoquinoline-4-yl)phenyl]urea, and 3-{4-[(6-chloro-3,4-dihydro-1-dimethylaminoisoquinolin-4-yl)phenyl]}imidazolidine-2,4-dione or a pharmaceutically acceptable salt or trifluoroacetate thereof.

6. A pharmaceutical composition comprising the compounds of formula I as recited in claim 1 and the suitable salts thereof in a pharmaceutically acceptable carrier comprised of one or more bulking agents, fillers, solvents, stabilizers, tableting agents, dissolution agents and mixtures thereof.

7. A pharmaceutical composition comprising the compounds of formula I as recited in claim 3 and the suitable salts thereof in a pharmaceutically acceptable carrier comprised of one or more bulking agents, fillers, solvents, stabilizers, tableting agents, dissolution agents and mixtures thereof.

8. A pharmaceutical composition comprising the compounds of formula I as recited in claim 5 and the suitable salts thereof in a pharmaceutically acceptable carrier comprised of one or more bulking agents, fillers, solvents, stabilizers, tableting agents, dissolution agents and mixtures thereof.

9. A pharmaceutical composition comprising the compound of the formula I and/or its pharmaceutically acceptable salts as recited in claim 1 in combination with one or more other active pharmaceuticals or ingredients in a pharmaceutically acceptable carrier composition.

10. A pharmaceutical composition comprising the compound of the formula I and/or its pharmaceutically acceptable salts as recited in claim 3 in combination with one or more other active pharmaceuticals or ingredients in a pharmaceutically acceptable carrier composition.

11. A pharmaceutical composition comprising the compound of the formula I and/or its pharmaceutically acceptable salts as recited in claim 5 in combination with one or more other active pharmaceuticals or ingredients in a pharmaceutically acceptable carrier composition.

* * * * *